US009969808B2

(12) United States Patent
van Eenennaam et al.

(10) Patent No.: US 9,969,808 B2
(45) Date of Patent: May 15, 2018

(54) ALTERED APRIL BINDING ANTIBODIES

(71) Applicant: ADURO BIOTECH HOLDINGS, EUROPE B.V., Oss (NL)

(72) Inventors: Hans van Eenennaam, Nijmegen (NL); Andrea van Elsas, Oss (NL); David Lutje Hulsik, Nijmegen (NL); Jan Paul Medema, Nieuw Vennep (NL)

(73) Assignee: ADURO BIOTECH HOLDINGS, EUROPE B.V., Oss (NL)

( * ) Notice: Subject to any disclaimer, the term of this patent is extended or adjusted under 35 U.S.C. 154(b) by 0 days. days.

(21) Appl. No.: 14/991,708

(22) Filed: Jan. 8, 2016

(65) Prior Publication Data
US 2016/0264674 A1 Sep. 15, 2016

(30) Foreign Application Priority Data

Jan. 9, 2015 (NL) ..................................... 2014108

(51) Int. Cl.
*C07K 16/28* (2006.01)
*A61K 39/395* (2006.01)
*A61K 45/06* (2006.01)
*G01N 33/564* (2006.01)
*G01N 33/574* (2006.01)
*A61K 39/00* (2006.01)

(52) U.S. Cl.
CPC ...... *C07K 16/2875* (2013.01); *A61K 39/3955* (2013.01); *A61K 45/06* (2013.01); *G01N 33/564* (2013.01); *G01N 33/57488* (2013.01); *A61K 2039/505* (2013.01); *C07K 2317/24* (2013.01); *C07K 2317/30* (2013.01); *C07K 2317/33* (2013.01); *C07K 2317/56* (2013.01); *C07K 2317/565* (2013.01); *C07K 2317/567* (2013.01); *C07K 2317/76* (2013.01); *C07K 2317/92* (2013.01); *C07K 2317/94* (2013.01); *G01N 2800/24* (2013.01)

(58) Field of Classification Search
CPC ............ C07K 16/2875; C07K 2317/24; C07K 2317/30; C07K 2317/33; C07K 2317/56; C07K 2317/565; C07K 2317/567; C07K 2317/76; C07K 2317/92; C07K 2317/94; A61K 45/06; A61K 39/3955; A61K 2039/505; G01N 33/488; G01N 33/564; G01N 2800/24
See application file for complete search history.

(56) References Cited

U.S. PATENT DOCUMENTS

| | | | |
|---|---|---|---|
| 4,816,567 A | 3/1989 | Cabilly et al. |
| 4,946,778 A | 8/1990 | Ladner et al. |
| 5,225,539 A | 7/1993 | Srivastava et al. |
| 5,260,203 A | 11/1993 | Ladner et al. |
| 5,624,821 A | 4/1997 | Winter et al. |

FOREIGN PATENT DOCUMENTS

| | | |
|---|---|---|
| EP | 404097 B1 | 9/1996 |
| WO | 8801649 A1 | 3/1988 |
| WO | 9311161 A1 | 6/1993 |
| WO | 9614328 A1 | 5/1996 |
| WO | 9900518 A1 | 1/1999 |
| WO | 9912965 A2 | 3/1999 |
| WO | 0160397 | 8/2001 |
| WO | 0160397 A2 | 8/2001 |
| WO | 0196528 A2 | 12/2001 |
| WO | 02094192 A2 | 11/2002 |
| WO | 03086310 A2 | 10/2003 |
| WO | 2005120571 A2 | 12/2005 |
| WO | 2008079246 A2 | 7/2008 |
| WO | 2010003108 A2 | 1/2010 |
| WO | 2010021697 A2 | 2/2010 |
| WO | 2010032061 A1 | 3/2010 |
| WO | 2010100056 A2 | 9/2010 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Milgrom, et al., Treatment of Allergic Asthma with Monoclonal Anti-IgE Antibody. rhuMAb-E25 Study Group. N Engl J Med. Dec. 23, 1999;341(26)1966-1973.
Moreaux et al, BAFF and APRIL protect myeloma cells from apoptosis induced by interleukin 6 deprivation and dexamethasone. Blood. Apr. 15, 2004;103(8):3148-3157.
Morrison et al., Chimeric human antibody molecules: mouse antigen-binding domains with human constant region domains. Proc Natl Acad Sci USA. Nov. 1984;81(21):6851-6855.
Nygren, Conjugation of Horseradish Peroxidase to Fab Fragments with Different Homobifunctional and Heterobifunctional Cross-Linking Reagents. A Comparative Study. J Histochem Cytochem. May 1982;30(5):407-412.
Pain and Surolia, Preparation of protein A-peroxidase monoconjugate using a heterobifunctional reagent, and its use in enzyme immunoassays. J Immunol Methods. 1981;40(2):219-230.
Planelles et al., APRIL but Not BLyS Serum Levels Are Increased in Chronic Lymphocytic Leukemia: Prognostic Relevance of APRIL for Survival. Haematologica. Sep. 2007;92(9):1284-1285.
Portielje et al., IL-12: a promising adjuvant for cancer vaccination. Cancer Immunol Immunother. Mar. 2003;52(3):133-144.
Presta, Selection, design, and engineering of therapeutic antibodies. J Allergy Clin Immunol. Oct. 2005;116(4):731-736.

(Continued)

*Primary Examiner* — Robert S Landsman
(74) *Attorney, Agent, or Firm* — Acuity Law Group, PC; Michael A. Whittaker

(57) ABSTRACT

The invention relates to APRIL-binding antibodies, which bind the same epitope of human APRIL as an antibody having an antigen binding site of hAPRIL.01A. The antibodies of the present invention comprise specific selections of framework sequences of the $V_H$ and $V_L$ domains and have unexpected features in comparison to hAPRIL.01A. The invention further relates to compositions comprising an antibody of the invention and to the medical and diagnostic uses of the antibodies and compositions.

26 Claims, 2 Drawing Sheets

(56) References Cited

OTHER PUBLICATIONS

Presta, Engineering of therapeutic antibodies to minimize immunogenicity and optimize function. Adv Drug Deliv Rev. Aug. 7, 2006;58(5-6):640-656.

Presta et al., Generation of a Humanized, High Affinity Anti-tissue Factor Antibody for Use as a Novel Antithrombotic Therapeutic. Thromb Haemost. Mar. 2001;85(3):379-389.

Roderburg et al., Serum concentrations of A Proliferation-Inducing Ligand (APRIL) are elevated in sepsis and predict mortality in critically ill patients. J Crit Care. Oct. 2013;28(5):882.e1-11.

Roschke et al., BLyS and APRIL Form Biologically Active Heterotrimers That Are Expressed in Patients with Systemic Immune-Based Rheumatic Diseases. J Immunol. Oct. 15, 2002;169(8):4314-4321.

Roth et al., APRIL, a new member of the tumor necrosis factor family, modulates death ligand-induced apoptosis. Cell Death Differ. Apr. 2001;8(4):403-410.

Schwaller et al., Neutrophil-derived APRIL concentrated in tumor lesions by proteoglycans correlates with human B-cell lymphoma aggressiveness. Blood. Jan. 1, 2007;109(1):331-8.

Slamon, et al., Use of Chemotherapy plus a Monoclonal Antibody against HER2 for Metastatic Breast Cancer That Overexpresses HER2. N Engl J Med. Mar. 15, 2001;344(11):783-792.

Slootstra et al., Structural aspects of antibody-antigen interaction revealed through small random peptide libraries. Mol Divers. Feb. 1996;1(2):87-96.

Stein et al., APRIL modulates B and T cell immunity. J Clin Invest. Jun. 2002;109(12):1587-1598.

Stohl, Therapeutic Targeting of B Lymphocyte Stimulator (BLyS) in the Rheumatic Diseases. Endocr Metab Immune Disord Drug Targets. Dec. 2006;6(4):351-358.

Suzuki et al., Physicochemical and biological properties of poly-(ethylene glycol)-coupled immunoglobulin G. Biochim Biophys Acta. Jul. 31, 1984;788(2):248-255.

Tai et al., 2014, A Novel Anti-a Proliferation-Inducing Ligand Hapril.01A Monoclonal Antibody Targets Multiple Myeloma Cells in the Bone Marrow Microenvironment. ASH poster 2098, 2014 (2 pages).

Tan et al., Local Production of B Lymphocyte Stimulator Protein and APRIL in Arthritic Joints of Patients With Inflammatory Arthritis. Arthritis Rheum. Apr. 2003;48(4):982-992.

Timmerman et al., Functional reconstruction and synthetic mimicry of a conformational epitope using CLIPS Technology. J Mol Recognit. Sep.-Oct. 2007;20(5):283-299.

Venkatramani et al., An Epidemiologically Significant Epitope of a 1998 Human Influenza Virus Neuraminidase Forms a Highly Hydrated Interface in the NA—Antibody Complex. J Mol Biol. Feb. 24, 2006;356(3):651-663.

Vincent and Zurini, Current strategies in antibody engineering: Fc engineering and pH-dependent antigen binding, bispecific antibodies and antibody drug conjugates. Biotechnol J. Dec. 2012;7(12):1444-1450.

Wallweber et al., The Crystal Structure of A Proliferation-inducing Ligand, APRIL. J Mol Biol. Oct. 15, 2004;343(2):283-290.

Yang, et al., Development of ABX-EGF, a fully human anti-EGF receptor monoclonal antibody, for cancer therapy. Crit Rev Oncol Hematol. Apr. 2001;38(1):17-23.

Yang, et al., A Randomized Trial of Bevacizumab, an Anti-Vascular Endothelial Growth Factor Antibody, for Metastatic Renal Cancer N Engl J Med. Jul. 31, 2003;349(5):427-434.

Ye et al., IgBLAST: an immunoglobulin variable domain sequence analysis tool. Nucleic Acids Res. Jul. 2013;41(Web Server issue):W34-40.

The International Search Report and Written Opinion issued in PCT/EP2016/050314 dated Feb. 26, 2016.

Guadagnoli et al., Development and characterization of APRIL antagonistic monoclonal antibodies for treatment of B-cell lymphomas. Blood. Jun. 23, 2011;117(25):6856-6865.

Altschul et al., Basic Local Alignment Search Tool. J Mol Biol. Oct. 5, 1990;215(3):403-410.

Anderson and Tomasi, Polymer modification of antibody to eliminate immune complex and Fc binding. J Immunol Methods. Apr. 22, 1988;109(1):37-42.

Angal et al., A single amino acid substitution abolishes the heterogeneity of chimeric mouse/human (IgG4) antibody. Mol Immunol. Jan. 1993;30(1):105-108.

Baert et al., Influence of Immunogenicity on the Long-Term Efficacy of Infliximab in Crohn's Disease. N Engl J Med. Feb. 13, 2003;348(7):601-608.

Beniaminovitz et al., Prevention of Rejection in Cardiac Transplantation by Blockade of the Interleukin-2 Receptor with a Monoclonal Antibody. N Engl J Med. Mar. 2, 2000;342(9):613-619.

Benson et al., GenBank. Nucleic Acids Res. Jan. 2013;41(Database issue):D36-42.

Berman et al., The Protein Data Bank. Nucleic Acids Res. Jan. 1, 2000;28(1)235-242.

Brekke and Sandlie, Therapeutic antibodies for human diseases at the dawn of the twenty-first century. Nat Rev Drug Discov. Jan. 2003;2(1):52-62.

Carnahan et al., Epratuzumab, a Humanized Monoclonal Antibody Targeting CD22: Characterization of in Vitro Properties. Clin Cancer Res. Sep. 1, 2003;9(10 Pt 2):3982S-3990S.

Carter et al., High level *Escherichia coli* expression and production of a bivalent humanized antibody fragment. Biotechnology (N Y). Feb. 1992;10(2):163-167.

Champe et al., Monoclonal Antibodies That Block the Activity of Leukocyte Function-associated Antigen 1 Recognize Three Discrete Epitopes in the Inserted Domain of CD11a. J Biol Chem. Jan. 20, 1995;270(3):1388-1394.

Chapman, PEGylated antibodies and antibody fragments for improved therapy: a review. Adv Drug Deliv Rev. Jun. 17, 2002;54(4):531-545.

Chothia and Leskl, Canonical Structures for the Hypervariable Regions of Immunoglobulins. J Mol Biol. Aug. 20, 1987;196(4):901-917.

Clackson et al., Making antibody fragments using phage display libraries. Nature. Aug. 15, 1991;352(6336):624-628.

Cunningham and Wells, High-Resolution Epitope Mapping of hGH-Receptor Interactions by Alanine-Scanning Mutagenesis. Science. Jun. 2, 1989;244(4908):1081-1085.

David and Reisfeld, Protein Iodination with Solid State Lactoperoxidase. Biochemistry. Feb. 26, 1974;13(5)1014-1021.

Deshayes et al., Abnormal production of the TNF-homologue APRIL increases the proliferation of human malignant glioblastoma cell lines via a specific receptor. Oncogene. Apr. 15, 2004;23(17):3005-3012.

Diebolder et al., Complement Is Activated by IgG Hexamers Assembled at the Cell Surface. Science. Mar. 14, 2014;343(6176):1260-1263.

Ding et al., 2013, Serum sAPRIL: A potential tumor-associated biomarker to colorectal cancer. Clin Biochem. Oct. 2013;46(15):1590-1594.

Foote and Winter, Antibody Framework Residues Affecting the Conformation of the Hypervariable Loops. J Mol Biol. Mar. 20, 1992;224(2):487-499.

Shosh, et al., Natalizumab for Active Crohn's Disease. N Engl J Med. Jan. 2, 2003;348(1):24-32.

Guss et al., Structure of the IgG-binding regions of streptococcal protein G. EMBO J. Jul. 1986;5(7):1567-1575.

Hahne et al., APRIL, a New Ligand of the Tumor Necrosis Factor Family, Stimulates Tumor Cell Growth. J Exp Med. Sep. 21, 1998;188(6):1185-1190.

Hardenberg et al., Thymus-independent class switch recombination is affected by APRIL. Immunol Cell Biol. Aug.-Sep. 2008; 86(6):530-534.

Hendriks et al., Heparan sulfate proteoglycan binding promotes APRIL-induced tumor cell proliferation. Cell Death Differ. Jun. 2005;12(6):637-648.

Herold et al., Anti-CD3 monoclonal antibody in new-onset type 1 diabetes mellitus. N Engl J Med. May 30, 2002;346(22):1692-1698.

(56) References Cited

OTHER PUBLICATIONS

Holliger and Hudson, Engineered antibody fragments and the rise of single domains. Nat Biotechnol. Sep. 2005;23(9):1126-1136.
Holliger et al., "Diabodies": Small bivalent and bispecific antibody fragments. Proc Natl Acad Sci U S A. Jul. 15, 1993;90(14):6444-6448.
Hunter and Greenwood, 1962, Preparation of Iodine-III Labelled Human Growth Hormone of High Specific Activity. Nature. May 5, 1962;194:495-496.
Jonsson et al., Symptomatic secondary Sjogren's syndrome in Patients with Systemic Lupus Erythematosus (SLE). Relation to anti-SS-A and anti-SS-B autoantibodies. Scand J Rheumatol Suppl. 1986;61:166-169.
Jordan et al., Structural understanding of stabilization patterns in engineered bispecific Ig-like antibody molecules. Proteins. Dec. 2009;77(4):832-841.
Kaneko and Niwa, Optimizing Therapeutic Antibody Function: Progress with Fc Domain Engineering. BioDrugs. Feb. 1, 2011;25(1):1-11.
Kim et al., Heavy and Light Chain Variable Single Domains of an Anti-DNA Binding Antibody Hydrolyze Both Double- and Single-stranded DNAs without Sequence Specificity. J Biol Chem. Jun. 2, 2006;281(22):15287-15295.
Kimberley et al., "APRIL Hath Put a Spring of Youth in Everything": Relevance of APRIL for Survival. J Cell Physiol. Jan. 2009;218(1):1-8.
Kohler and Milstein, Continuous cultures of fused cells secreting antibody of predefined specificity. Nature. Aug. 7, 1975;256(5517):495-497.
Konagurthu et al., Mustang: A Multiple Structural Alignment Algorithm. Proteins. Aug. 15, 2006;64(3):559-574.
Koyama et al., Raised serum APRIL levels in patients with systemic lupus erythematosus. Ann Rheum Dis. Jul. 2005;64(7):1065-1067.
Krieger et al., Homology Modeling. Methods Biochem Anal. 2003;44:509-523.

Labrijn et al., Efficient generation of stable bispecific IgG1 by controlled Fab-arm exchange. Proc Natl Acad Sci U S A. Mar. 26, 2013;110(13):5145-5150.
Lascano et al., Chronic lymphocytic leukemia disease progression is accelerated by APRIL-TACI interaction in the TCL1 transgenic mouse model. Blood. Dec. 5, 2013;122(24):3960-3963.
Lee et al., Heterosubtypic antibody recognition of the influenza virus hemagglutinin receptor binding site enhanced by avidity. Proc Natl Acad Sci USA. Oct. 16, 2012;109(42):17040-17045.
LeFranc et al., IMGT, the international ImMunoGeneTics database. Nucleic Acids Res. Jan. 1, 1999;27(1):209-212.
Li et al., New targets of PS-341: BAFF and APRIL. Med Oncol. Jun. 2010;27(2):439-445.
Lindmark et al., Binding of Immunoglobulins to Protein A and Immunoglobulin Levels in Mammalian Sera. J Immunol Methods. Aug. 12, 1983;62(1):1-13.
Lipsky, et al., Infliximab and methotrexate in the treatment of rheumatoid arthritis. Anti-Tumor Necrosis Factor Trial in Rheumatoid Arthritis with Concomitant Therapy Study Group. N Engl J Med. Nov. 30, 2000;343(22):1594-1602.
Liu and Blumhardt, Randomised, double blind, placebo controlled study of interferon β-1a in relapsing-remitting multiple sclerosis analysed by area under disability/time curves. J Neurol Neurosurg Psychiatry. Oct. 1999;67(4):451-456.
Lopez-Fraga et al., Biologically active APRIL is secreted following intracellular processing in the Golgi apparatus by furin convertase. EMBO Rep. Oct. 2001;2(10):945-951.
Marks et al., By-passing Immunization. Human antibodies from V-gene Libraries Displayed on Phage. J Mol Biol. Dec. 5, 1991;222(3):581-597.
Matsushita et al., Elevated serum levels of APRIL, but not BAFF, in patients with atopic dermatitis. Exp Dermatol. Mar. 2008;17(3):197-202.
McCarthy et al., Mice overexpressing Baff develop a commensal flora-dependent, IgA-associated nephropathy. J Clin Invest. Oct. 2011;121(10):3991-4002.

* cited by examiner

ALTERED APRIL BINDING ANTIBODIES

CROSS-REFERENCE TO RELATED APPLICATIONS

The present invention claims priority to Dutch Patent Application No. NL 2014108, filed Jan. 9, 2015, which is hereby incorporated in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Jan. 8, 2016, is named ABE0001UT_SeqListing.txt and is 73 kilobytes in size.

FIELD OF THE INVENTION

The present invention relates to isolated antibodies, including fragments thereof, which bind human APRIL, to polynucleotides encoding such antibodies and host cells producing said antibodies. The antibodies can be used to treat cancers and inhibit immune cell proliferation and conditions that may benefit from such inhibition of immune cell proliferation such as autoimmune diseases, inflammatory diseases, or diseases associated with immunoglobulin over production. In addition, the antibodies can be used as diagnostic tool and in vitro agents for inhibition of immune cell proliferation and/or survival.

BACKGROUND OF THE INVENTION

APRIL is expressed as a type-II transmembrane protein, but unlike most other TNF family members it is mainly processed as a secreted protein and cleaved in the Golgi apparatus where it is cleaved by a furin convertase to release a soluble active form (Lopez-Fraga et al., 2001, *EMBO Rep* 2:945-51,). APRIL assembles as a non-covalently linked homo-trimer with similar structural homology in protein fold to a number of other TNF family ligands (Wallweber et al., 2004, *Mol Biol* 343, 283-90). APRIL binds two TNF receptors: B cell maturation antigen (BCMA) and transmembrane activator and calcium modulator and cyclophilin ligand interactor (TACI) (reviewed in Kimberley et al., 2009, *J Cell Physiol.* 218(1):1-8). In addition, APRIL has recently been shown to bind heparan sulphate proteoglycans (HSPGs) (Hendriks et al., 2005, *Cell Death Differ* 12, 637-48). APRIL has been shown to have a role in B cell signalling and drive both proliferation and survival of human and murine B cells in-vitro (reviewed in Kimberley et al., 2009, *J Cell Physiol.* 218(1):1-8).

APRIL is predominantly expressed by immune cell subsets such as monocytes, macrophages, dendritic cells, neutrophils, B-cells, and T-cells, many of which also express BAFF. In addition, APRIL can be expressed by non-immune cells such as osteoclasts, epithelial cells and a variety of tumour tissues (reviewed in Kimberley et al., 2009, *J Cell Physiol.* 218(1):1-8). In fact, APRIL was originally identified based on its expression in cancer cells (Hahne et al., 1998, *J Exp Med* 188, 1185-90). High expression levels of APRIL mRNA were found in a panel of tumour cell lines as well as human primary tumours such as colon, and a lymphoid carcinoma.

A retrospective study under 95 Chronic Lymphocytic Leukaemia (CLL) CLL patients showed increased levels of APRIL in serum, which correlated with disease progression and overall patient survival, with a poorer prognosis for patients with high APRIL serum levels (Planelles et al., 2007, *Haematologica* 92, 1284-5). Similarly, (increased levels of) APRIL was shown to be expressed in Hodgkin's lymphoma, Non-Hodgkin's lymphoma (NHL) and Multiple Myeloma (MM) (reviewed in Kimberley et al., 2009, *J Cell Physiol.* 218(1):1-8). A retrospective study in DLBCL patients (NHL) showed that high APRIL expression in cancer lesions correlated with a poor survival rate (Schwaller et al., 2007, *Blood* 109, 331-8). Recently, APRIL serum levels in serum from patients suffering from colorectal cancer were shown to have a positive diagnostic value (Ding et al., 2013, Clin. Biochemistry, http://dx.doi.org/10.1016/j. clinbiochem.2013.06.008).

Due to its role in B cell biology APRIL also plays a role in many autoimmune diseases. Increased serum levels of APRIL have been reported in many SLE patients (Koyama et al., 2005, *Ann Rheum Dis* 64, 1065-7). A retrospective analysis revealed that APRIL serum levels tended to correlate with anti-dsDNA antibody titres. Also in the synovial fluid of patients with inflammatory arthritis significantly increased APRIL levels as compared with those with patients suffering from non-inflammatory arthritis such as osteoarthritis were detected (Stohl et al., 2006, *Endocr Metab Immune Disord Drug Targets* 6, 351-8; Tan et al., 2003, *Arthritis Rheum* 48, 982-92).

Several studies focused on the presence of APRIL in the sera of patients suffering from a wider range of systemic immune-based rheumatic diseases (now also including Sjögren's syndrome, Reiter's syndrome, psoriatic arthritis, polymyositis, and ankylosing spondylitis) and found significantly increased APRIL levels in these patients, suggesting an important role for APRIL in these diseases as well (Jonsson et al., 1986, Scand J Rheumatol Suppl 61, 166-9; Roschke et al., 2002, J Immunol 169, 4314-21). In addition, increased APRIL serum levels were detected in serum from patients suffering atopic dermatitis (Matsushita et al., 2007, Exp. Dermatology 17, 197-202). Also, serum APRIL levels are elevated in sepsis and predict mortality in critically ill patients (Roderburg et al., J. Critical Care, 2013, dx.doi.org/10.1016/j.jcrc.2012.11.007). Furthermore, APRIL serum levels were found to be increased in patients suffering from IgA nephropathy (McCarthy et al., 2011, J. Clin. Invest. 121(10):3991-4002).

Finally, increased APRIL expression has also been linked to Multiple Sclerosis (MS). APRIL expression was found to be increased in the astrocytes of MS sufferers compared with normal controls. This is in line with the described APRIL expression in glioblastomas and in the serum of glioblastoma patients (Deshayes et al., 2004, *Oncogene* 23, 3005-12; Roth et al., 2001, *Cell Death Differ* 8, 403-10).

APRIL plays a crucial role in the survival and proliferative capacity of several B-cell malignancies, and potentially also some solid tumours. APRIL is also emerging as a key player in inflammatory diseases or autoimmunity. Thus, strategies to antagonise APRIL are a therapeutic goal for a number of these diseases. Indeed clinical studies targeting APRIL with TACI-Fc (Atacicept) are currently ongoing for treatment of several autoimmune diseases. However, TACI-Fc also targets BAFF, a factor involved in normal B-cell maintenance. Antibodies directed against APRIL have been described in WO9614328, WO2001/60397, WO2002/94192, WO9912965, WO2001/196528, WO9900518 and WO2010/100056. WO2010/100056 describes antibodies targeting APRIL specifically. The antibodies of WO2010/100056 fully block the binding of APRIL to TACI and at least partially to BCMA. Antibody hAPRIL.01A fully blocks the binding to both BCMA and TACI. The hAPRIL.01A antibody inhibited B-cell proliferation, survival and antigen-specific Immunoglobulin secretion in vitro and in vivo (Guadagnoli et al., 2011, *Blood* 117(25):6856-65). In addition, hAPRIL.01A inhibited proliferation and survival of malignant cells in in vitro and in vivo representative of human CLL and MM disease (Guadagnoli et al., 2011, *Blood* 117(25):6856-65; Lascano et al., 2013, Blood 122(24): 3960-3; Tai et al., 2014, ASH poster 2098). Finally, hAPRIL.01A inhibited the secretion of antigen-specific IgA (Guadagnoli et al., 2011, *Blood* 117(25):6856-65). In view of these unique binding features this murine antibody has a unique pharmaceutical utility. However, in view of its murine origin there are also certain drawbacks in the pharmaceutical utility of this antibody in human medicine. The present invention therefore is aimed at providing altered hAPRIL.01A antibodies more suitable for use in human medicine.

SUMMARY OF THE INVENTION

The present invention provides hAPRIL.01A analogues comprising certain substitutions of the framework regions of the $V_H$ and $V_L$ domains. It has been surprisingly found that when in an antigen binding site of hAPRIL.01A the framework regions of the $V_H$ domain of hAPRIL.01A are substituted for framework regions from a $V_H$ amino acid sequence selected from SEQ ID NO 12, 14, 16 or 18 and the framework regions of the $V_L$ domain of hAPRIL.01A are substituted for the framework regions of a $V_L$ amino acid sequence selected from SEQ ID NO 30, functional hAPRIL.01A analogues are obtained. This is surprising in view of the fact that research by the inventors of the present invention has shown, that only limited combinations of alternative $V_H$ and $V_L$ framework sequences from human origin can support adequate binding of the hAPRIL.01A CDRs to human APRIL and thus can result in functional hAPRIL.01A analogues. In addition the inventors of the present invention have shown that further improvements in the hAPRIL.01 analogues may be obtained by introducing certain specific amino acid substitutions. In particular amino acid substitution R72S and/or the double substitution R67K in combination with V68A in a selected $V_H$ amino acid sequence.

The invention thus according to a first aspect relates to an APRIL-binding antibody, binding to the same epitope of human APRIL as an antibody, having an antigen binding site of hAPRIL.01A, such as monoclonal antibody hAPRIL.01A disclosed in WO2010/100056, said human APRIL-binding antibody comprising a number of antigen binding sites comprising $V_H$ and $V_L$ domains, wherein in an antigen binding site the framework sequences of the $V_H$ domain have at least 70% sequence similarity with the framework sequences of a $V_H$ amino acid sequence selected from SEQ ID NO: 12, 14, 16 or 18, preferably with SEQ ID NO: 14 or 18, most preferably SEQ ID NO: 18, and the framework sequences of the $V_L$ domain have at least 70% sequence similarity with the framework sequences of a $V_L$ amino acid sequence selected from SEQ ID NO: 30.

Further aspect of the invention relate to polynucleotides, in isolated form, coding for the variable region of the heavy chain and light chain of the antibody of the invention, an expression unit comprising a number of the polynucleotides and a host cell comprising the expression unit and/or a number of the polynucleotides.

Yet a further aspect of the invention relates to a method of producing an antibody of the invention, which method comprises:

a) culturing a host cell of the invention in culture medium under conditions wherein the number of polynucleotides is expressed, thereby producing polypeptides comprising the light and heavy chain variable regions; and b) recovering the polypeptides from the host cell or culture medium.

A composition comprising an antibody of the invention in combination with a pharmaceutically acceptable carrier or diluent and optionally a number of other active compounds is the subject of a further aspect of the invention.

The therapeutic and diagnostic use of the antibody of the invention is yet another aspect of the present invention.

BRIEF DESCRIPTION OF THE SEQUENCES

The sequences presented in the sequence listing relate to the amino acid sequences and encoding DNA sequences of $V_H$ and $V_L$ domains and of heavy and light chains from which framework sequences may be employed in the antibodies according to the invention. In addition the amino acid sequences of the CDRs of both the $V_H$ and $V_L$ domains of hAPRIL.01A and of the heavy and light chains are presented. According to certain embodiments of the invention CDRs of hAPRIL.01A are employed in the antibody of the invention. Table 1 below correlates the sequence IDs to their respective sequence.

TABLE 1

Sequence Listing

| SEQ ID NO: | Description |
|---|---|
| 1 | hAPRIL.01A heavy chain variable region (DNA) |
| 2 | hAPRIL.01A light chain variable region (DNA) |
| 3 | hAPRIL.01A heavy chain variable region (AA) |
| 4 | hAPRIL.01A light chain variable region (AA) |
| 5 | hAPRIL.01A heavy chain CDR1 (AA) |
| 6 | hAPRIL.01A heavy chain CDR2 (AA) |
| 7 | hAPRIL.01A heavy chain CDR3 (AA) |
| 8 | hAPRIL.01A light chain CDR1 (AA) |
| 9 | hAPRIL.01A light chain CDR2 (AA) |
| 10 | hAPRIL.01A light chain CDR3 (AA) |
| 11 | VH11 heavy chain variable region (DNA) |
| 12 | VH11 heavy chain variable region (AA) |
| 13 | VH12 heavy chain variable region (DNA) |
| 14 | VH12 heavy chain variable region (AA) |
| 15 | VH13 heavy chain variable region (DNA) |
| 16 | VH13 heavy chain variable region (AA) |
| 17 | VH14 heavy chain variable region (DNA) |
| 18 | VH14 heavy chain variable region (AA) |
| 19 | VL10 light chain variable region (DNA) |
| 20 | VL10 light chain variable region (AA) |
| 21 | VL11 light chain variable region (DNA) |
| 22 | VL11 light chain variable region (AA) |
| 23 | VL12 light chain variable region (DNA) |
| 24 | VL12 light chain variable region (AA) |
| 25 | VL13 light chain variable region (DNA) |
| 26 | VL13 light chain variable region (AA) |
| 27 | VL14 light chain variable region (DNA) |
| 28 | VL14 light chain variable region (AA) |
| 29 | VL15 light chain variable region (DNA) |
| 30 | VL15 light chain variable region (AA) |
| 31 | VH14_1 heavy chain variable region (DNA) |
| 32 | VH14_1 heavy chain variable region (AA) |
| 33 | VH14_1C heavy chain variable region (DNA) |
| 34 | VH14_1C heavy chain variable region (AA) |
| 35 | VH14_1D heavy chain variable region (DNA) |
| 36 | VH14_1D heavy chain variable region (AA) |
| 37 | VH14_1E heavy chain variable region (DNA) |

TABLE 1-continued

Sequence Listing

| SEQ ID NO: | Description |
|---|---|
| 38 | VH14_1E heavy chain variable region (AA) |
| 39 | VH14_1G heavy chain variable region (DNA) |
| 40 | VH14_1G heavy chain variable region (AA) |
| 41 | VH11 heavy chain (DNA) |
| 42 | VH11 heavy chain (AA) |
| 43 | VH12 heavy chain (DNA) |
| 44 | VH12 heavy chain (AA) |
| 45 | VH13 heavy chain (DNA) |
| 46 | VH13 heavy chain (AA) |
| 47 | VH14 heavy chain (DNA) |
| 48 | VH14 heavy chain (AA) |
| 49 | VL15 light chain (DNA) |
| 50 | VL15 light chain (AA) |
| 51 | VH14_1G heavy chain (DNA) |
| 52 | VH14_1G heavy chain (AA) |
| 53 | hAPRIL.01A heavy chain (DNA) |
| 54 | hAPRIL.01A light chain (DNA) |
| 55 | hAPRIL.01A heavy chain (AA) |
| 56 | hAPRIL.01A light chain (AA) |
| 57 | Heavy chain secretion leader sequence (DNA) |
| 58 | Heavy chain secretion leader sequence (AA) |
| 59 | Light chain secretion leader sequence (DNA) |
| 60 | Light chain secretion leader sequence (AA) |

SEQ ID NO: 11-52 relate to engineered immunoglobulin VH, VL, heavy or light chain sequences as indicated.

BRIEF DESCRIPTION OF THE FIGURES

FIG. 1A shows immunoglobulin titres (IgA1) resulting from targeting APRIL with hAPRIL.01A or the analogue 14_1G.15 in an in vivo test for T-cell independent B cell response. Transgenic mice (APRIL-Tg) were challenged with 250 µg NP-Ficoll (day 0), and treated with hAPRIL.01A or 14_1G.15 on day −1 and 3. PBS and wildtype mice (WT) were used as negative controls. The immunoglobulin titres were measured by ELISA. FIG. 1B shows immunoglobulin titres (IgA2)-resulting from targeting APRIL with hAPRIL.01A or the analogue 14_1G.15 in an in vivo test for T-cell independent B cell response. Transgenic mice (APRIL-Tg) were challenged with 250 µg NP-Ficoll (day 0), and treated with hAPRIL.01A or 14_1G.15 on day −1 and 3. PBS and wildtype mice (WT) were used as negative controls. The immunoglobulin titres were measured by ELISA. FIG. 1C shows immunoglobulin titres (IgG)-resulting from targeting APRIL with hAPRIL.01A or the analogue 14_1G.15 in an in vivo test for T-cell independent B cell response. Transgenic mice (APRIL-Tg) were challenged with 250 µg NP-Ficoll (day 0), and treated with hAPRIL.01A or 14_1G.15 on day −1 and 3. PBS and wildtype mice (WT) were used as negative controls. The immunoglobulin titres were measured by ELISA. FIG. 1D shows immunoglobulin titres (IgM) resulting from targeting APRIL with hAPRIL.01A or the analogue 14_1G.15 in an in vivo test for T-cell independent B cell response. Transgenic mice (APRIL-Tg) were challenged with 250 µg NP-Ficoll (day 0), and treated with hAPRIL.01A or 14_1G.15 on day −1 and 3. PBS and wildtype mice (WT) were used as negative controls. The immunoglobulin titres were measured by ELISA.

DETAILED DESCRIPTION

Figure 1A:
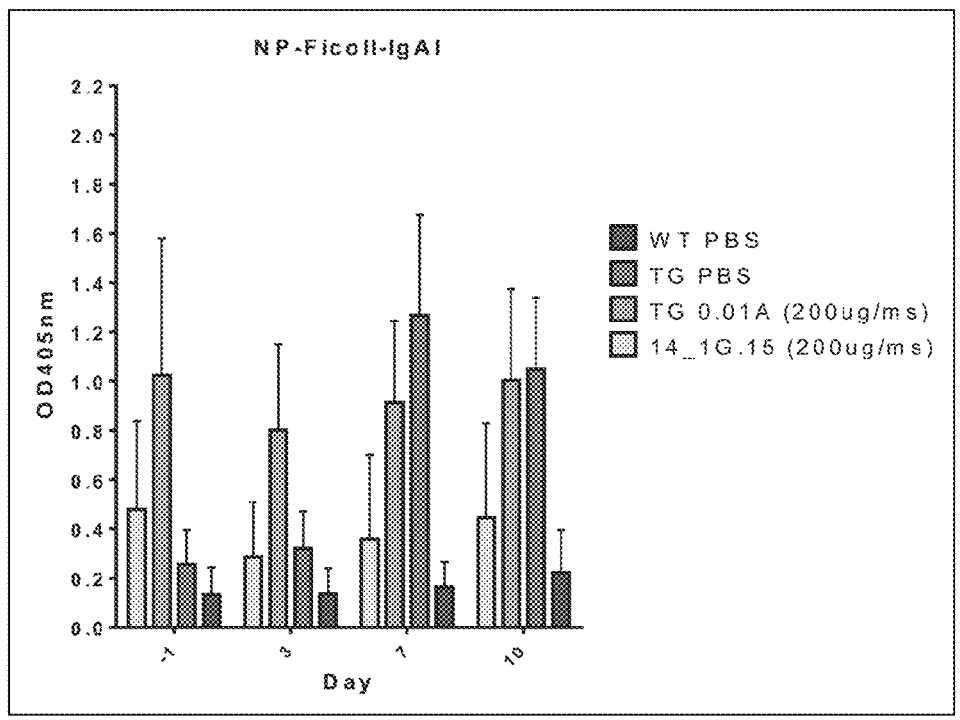
FIGS. 1A-1D.

The invention thus relates to antibodies that bind to the same epitope of human APRIL as an antibody, including an antibody analog, such as an antibody fragment, having an antigen binding site of hAPRIL.01A. The antibody hAPRIL.01A has been disclosed in WO2010/100056 with sequences of $V_H$ and $V_L$ domains and CDRs. The inventors of the present invention have found that there are limited possibilities to substitute the mouse framework region of the $V_H$ and $V_L$ domains of hAPRIL.01A by human alternatives. In addition the selected alternative framework sequences results in alternative anti-human APRIL antibodies having unexpected features. It is believed that the selected framework sequences manifest their special features within the context of binding to the human APRIL epitope for hAPRIL.01A and thus have a broad utility within this context. Therefore, the present invention is aimed at any antibody (including fragments and/or derivatives and/or analogues) that binds to the same epitope as hAPRIL.01A and which comprises the selected framework sequences in its $V_H$ and $V_L$ domains. In certain embodiments such an antibody will comprise alternative CDRs different from the CDRs of hAPRIL.01A. However, according to other embodiments the antibody will comprise CDRs similar to or even identical to those of hAPRIL.01A. According to certain embodiments an antibody comprising the $V_H$ domain CDR1, CDR2 and CDR3 and the $V_L$ domain CDR1, CDR2 and CDR3 of hAPRIL.01A or variants of any of said sequences is to be considered an antibody, binding to the same epitope of human APRIL as monoclonal antibody hAPRIL.01A. This in particular when it binds human APRIL with a $K_D$ of about 100 nM or lower and/or blocks binding of human APRIL to human BCMA and TACI with an $IC_{50}$ of about 100 nM or lower. Within the present invention preferred antibodies bind human APRIL with a $K_D$ value of about 100 nM or lower, such as within an interval selected from 100-0.001 nM, for example 100-0.010, 100-0.050, 100-0.100, 100-0.150, 100-0.200, 100-0.250, 100-0.300, 100-0.350, 100-0.400, 100-0.450, 90-0.500, 80-0.550, 70-0.600, 60-0.650, 50-0.700, 40-0.750, 30-0.800, 20-0.850, 10-0.900 or 1.0-0.950 nM. As the skilled person will understand lower values are preferred for the $K_D$, such as values below 50, 20, 10, 1.00 nM. Antibodies having $K_D$ values within such intervals are suitable for clinical applications (See, e.g. Presta, et al., 2001, Thromb. Haemost. 85:379-389; Yang, et al., 2001, Crit. Rev. Oncol. Hematol. 38:17-23; Carnahan, et al., 2003, Clin. Cancer Res. (Suppl.) 9:3982s-3990s). Antibody affinities may be determined using standard analysis known to the skilled person, for example as exemplified in the experimental section.

It is further preferred if an antibody of the invention blocks binding of human APRIL to human BCMA and TACI with an $IC_{50}$ value of about 100 nM or lower, such as within an interval selected from 100-0.001 nM, for example 100-0.010, 100-0.050, 100-0.100, 100-0.150, 100-0.200, 100-0.250, 100-0.300, 100-0.350, 100-0.400, 100-0.450, 90-0.500, 80-0.550, 70-0.600, 60-0.650, 50-0.700, 40-0.750, 30-0.800, 20-0.850, 10-0.900 or 1.0-0.950 nM. As the skilled person will understand lower values are preferred for the $IC_{50}$, such as values below 50, 20, 10, 1.00 nM.

Binding of the antibody to the same epitope as hAPRIL.01A may be evaluated by assessing the binding competition for human APRIL of an antibody of the present invention and a reference antibody having an antigen binding site of hAPRIL.01A in accordance with the methods presented in example 2 or 5 of WO2010/100056 or other cross-blocking or epitope mapping techniques known to the skilled person as discussed below. The antigen binding site of hAPRIL.01A is defined by the $V_H$ and $V_L$ domains as presented in SEQ ID NO: 3 and 4. Thus any antibody, including an antibody analog, such as an antibody fragment comprising the $V_H$ and $V_L$ domains as presented in SEQ ID NO: 3 and 4 may be used as a reference antibody for evaluating the binding to the same epitope of human APRIL as hAPRIL.01A. Antibody hAPRIL.01A, disclosed in WO2010/100056 is an example of an antibody having an antigen binding site of hAPRIL.01A and is a suitable reference antibody within the context of the present invention. However, also antibody fragments, such as Fab, F(ab)$_2$ or Fv fragments derived from hAPRIL.01A may be used as a reference antibody. Based on the DNA sequences of SEQ ID NO: 1 and 2 and the amino acid sequences of SEQ ID NO: 3 and 4, the skilled person will be able to construct and produce such antibody fragments derived from hAPRIL.01A. Based on the provided sequences the skilled person will also be able to produce hAPRIL.01A analogs for use as reference antibodies by joining the heavy chain variable region amino acid sequence of SEQ ID NO: 3 (coded by SEQ ID NO: 1) to the IgG1 constant region (from the mouse or from a different species, preferably from the mouse) and joining the light chain variable region amino acid sequence of SEQ ID NO: 4 (coded by SEQ ID NO: 2) to the κ constant region (from the mouse or from a different species, preferably from the mouse).

When evaluated with such methods, antibodies binding to the same epitope of human APRIL as hAPRIL.01A may block binding of a reference antibody having an hAPRIL.01A antigen binding site to human APRIL with an IC$_{50}$ of about 100 nM or lower, such as within an interval selected from 100-0.001 nM, for example 100-0.010, 100-0.050, 100-0.100, 100-0.150, 100-0.200, 100-0.250, 100-0.300, 100-0.350, 100-0.400, 100-0.450, 90-0.500, 80-0.550, 70-0.600, 60-0.650, 50-0.700, 40-0.750, 30-0.800, 20-0.850, 10-0.900 or 1.0-0.950 nM. As the skilled person will understand lower values are preferred for the IC$_{50}$, such as values below 50, 20, 10, 1.00 nM.

The antibody of the invention thus may have one or more of the following features:
 (i) binds human APRIL with a K$_D$ of about 100 nM or lower;
 (ii) blocks binding of human APRIL to human BCMA and human TACI with an IC$_{50}$ of about 100 nM or lower;
 (iii) blocks binding of hAPRIL.01A to human APRIL with an IC$_{50}$ of about 100 nM or lower.

These features may be combined in the following combinations: (i) or (ii) or (iii); (i) and (ii); (i) and (iii); (ii) and (iii); (i) and (ii) and (iii).

According to the present invention the framework sequences of the $V_H$ domain of an antigen binding site of the antibody are selected such that they have at least 70% sequence similarity with the framework sequences of a $V_H$ amino acid sequence selected from SEQ ID NO. 12, 14, 16 or 18. According to a preferred embodiment the framework sequences of a $V_H$ domain of the antibody are selected such that they have at least 70% sequence similarity with the framework sequences of a $V_H$ amino acid sequence selected from SEQ ID NO. 14 or 18, most preferably SEQ ID NO: 18. The framework sequences of the $V_L$ domain in said antigen binding site of the antibody are selected such that they have at least 70% sequence similarity with the framework sequences of a $V_L$ amino acid sequence selected from SEQ ID NO. 30.

The $V_H$ amino acid sequence selected from SEQ ID NO. 12, 14, 16 or 18 and the $V_L$ amino acid sequence selected from SEQ ID NO. 30, comprise both framework sequences and CDR sequences. The CDR sequences incorporated in these $V_H$ and $V_L$ amino acid sequences are those of hAPRIL.01A, and correspond to SEQ ID NO. 5 (hAPRIL.01A $V_H$ CDR1), 6 (hAPRIL.01A $V_H$ CDR2), 7 (hAPRIL.01A $V_H$ CDR3), 8 (hAPRIL.01A $V_L$ CDR1), 9 (hAPRIL.01A $V_L$ CDR2), 10 (hAPRIL.01A $V_L$ CDR3). However, as already stated above, the use of the $V_H$ and $V_L$ framework sequences, as selected within the present invention, is not restricted to combination with the specific CDRs of hAPRIL.01A. Thus the sequence similarity of at least 70% according to certain embodiments is to be considered for the framework sequences only and not for the full $V_H$ amino acid sequence as selected from SEQ ID NO. 12, 14, 16, 18, or the full $V_L$ amino acid sequence as selected from SEQ ID NO. 30. The framework sequences for the $V_H$ amino acid sequences as presented in SEQ ID NO. 12, 14, 16 or 18 are the parts of these sequences outside the $V_H$ CDRs i.e. the parts outside the sequence parts identical to SEQ ID NO. 5 (hAPRIL.01A $V_H$ CDR1), 6 (hAPRIL.01A $V_H$ CDR2), 7 (hAPRIL.01A $V_H$ CDR3). The framework sequences for the $V_L$ amino acid sequence as presented in SEQ ID NO. 30 are the parts of this sequence outside the $V_L$ CDRs i.e. the parts outside the sequence parts identical to SEQ ID NO. 8 (hAPRIL.01A $V_L$ CDR1), 9 (hAPRIL.01A $V_L$ CDR2), 10 (hAPRIL.01A $V_L$ CDR3).

According to alternative embodiments the sequence similarity of at least 70% is to be considered for the full $V_H$ amino acid sequence as selected from SEQ ID NO. 12, 14, 16 or 18 and the full $V_L$ amino acid sequence as selected from SEQ ID NO. 30.

Within the description of the present invention at least 70% sequence similarity should be understood as meaning at least 80%, such as at least 85%, preferably at least 90%, more preferably at least 95%, such as at least 99% sequence similarity.

As the skilled person will understand, "sequence similarity" refers to the extent to which individual nucleotide or peptide sequences are alike. The extent of similarity between two sequences is based on the extent of identity combined with the extent of conservative changes. The percentage of "sequence similarity" is the percentage of amino acids or nucleotides which is either identical or conservatively changed viz. "sequence similarity"=(% sequence identity)+(% conservative changes).

For the purpose of this invention "conservative changes" and "identity" are considered to be species of the broader term "similarity". Thus, whenever the term sequence "similarity" is used it embraces sequence "identity" and "conservative changes". According to certain embodiments the conservative changes are disregarded and the % sequence similarity refers to % sequence identity.

The term "sequence identity" is known to the skilled person. In order to determine the degree of sequence identity shared by two amino acid sequences or by two nucleic acid sequences, the sequences are aligned for optimal comparison purposes (e.g., gaps can be introduced in the sequence of a first amino acid or nucleic acid sequence for optimal alignment with a second amino or nucleic acid sequence). Such alignment may be carried out over the full lengths of the sequences being compared. Alternatively, the alignment may be carried out over a shorter comparison length, for example over about 20, about 50, about 100 or more nucleic acids/bases or amino acids.

The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The degree of identity shared between sequences is typically expressed in terms of percentage identity between the two sequences and is a function of the number of identical positions shared by identical residues in the sequences (i.e., % identity=number of identical residues at corresponding positions/total number of positions×100). Preferably, the two sequences being compared are of the same or substantially the same length.

The percentage of "conservative changes" may be determined similar to the percentage of sequence identity. However, in this case changes at a specific location of an amino acid or nucleotide sequence that are likely to preserve the functional properties of the original residue are scored as if no change occurred.

For amino acid sequences the relevant functional properties are the physico-chemical properties of the amino acids. A conservative substitution for an amino acid in a polypeptide of the invention may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without substantially altering the activity of a protein, particularly in regions of the protein that are not directly associated with biological activity (see, e.g., Watson, et al., *Molecular Biology of the Gene*, The Benjamin/Cummings Pub. Co., p. 224 (4th Edition 1987)). For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr and vice versa so that a free —OH is maintained; and Gln for Asn and vice versa to maintain a free —NH$_2$.

Exemplary conservative substitutions in the amino acid sequence of the CD70 binding peptides of the invention can be made in accordance with those set forth below as follows:

TABLE 2

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

For nucleotide sequences the relevant functional properties is mainly the biological information that a certain nucleotide carries within the open reading frame of the sequence in relation to the transcription and/or translation machinery. It is common knowledge that the genetic code has degeneracy (or redundancy) and that multiple codons may carry the same information in respect of the amino acid for which they code. For example in certain species the amino acid leucine is coded by UUA, UUG, CUU, CUC, CUA, CUG codons (or TTA, TTG, CTT, CTC, CTA, CTG for DNA), and the amino acid serine is specified by UCA, UCG, UCC, UCU, AGU, AGC (or TCA, TCG, TCC, TCT, AGT, AGC for DNA). Nucleotide changes that do not alter the translated information are considered conservative changes.

The skilled person will be aware of the fact that several different computer programs, using different mathematical algorithms, are available to determine the identity between two sequences. For instance, use can be made of a computer program employing the Needleman and Wunsch algorithm (Needleman et al. (1970)). According to an embodiment the computer program is the GAP program in the Accelrys GCG software package (Accelrys Inc., San Diego U.S. A). Substitution matrices that may be used are for example a BLOSUM 62 matrix or a PAM250 matrix, with a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

According to an embodiment the percent identity between two nucleotide sequences is determined using the GAP program in the Accelrys GCG software package (Accelrys Inc., San Diego U.S. A) A NWSgapdna CMP matrix and a gap weight of 40, 50, 60, 70, or 80 and a length weight of 1, 2, 3, 4, 5, or 6 is used.

In another embodiment, the percent identity of two amino acid or nucleotide sequences is determined using the algorithm of E. Meyers and W. Miller (Meyers et al. (1989)) which has been incorporated into the ALIGN program (version 2.0) (available at the ALIGN Query using sequence data of the Genestream server IGH Montpellier France xylian.igh.cnrs.fr/bin/align-guess.cgi) using a PAM120 weight residue table, a gap length penalty of 12 and a gap penalty of 4.

For the present invention it is most preferred to use BLAST (Basic Local Alignment Tool) to determine the percentage identity and/or similarity between nucleotide or amino acid sequences.

Queries using the BLASTn, BLASTp, BLASTx, tBLASTn and tBLASTx programs of Altschul et al. (1990) may be posted via the online versions of BLAST accessible via http://www.ncbi.nlm.nih.gov. Alternatively a standalone version of BLAST {e.g., version 2.2.29 (released 3 Jan. 2014)) downloadable also via the NCBI internet site may be used. Preferably BLAST queries are performed with the following parameters. To determine the percentage identity and/or similarity between amino acid sequences: algorithm: blastp; word size: 3; scoring matrix: BLOSUM62; gap costs: Existence: 11, Extension: 1; compositional adjustments: conditional compositional score matrix adjustment; filter: off; mask: off. To determine the percentage identity and/or similarity between nucleotide sequences: algorithm: blastn; word size: 11; max matches in query range: 0; match/mismatch scores: 2, −3; gap costs: Existence: 5, Extension: 2; filter: low complexity regions; mask: mask for lookup table only.

The percentage of "conservative changes" may be determined similar to the percentage of sequence identity with the aid of the indicated algorithms and computer programs. Some computer programs, e.g., BLASTp, present the number/percentage of positives (=similarity) and the number/percentage of identity. The percentage of conservative changes may be derived therefrom by subtracting the percentage of identity from the percentage of positives/similarity (percentage conservative changes=percentage similarity−percentage identity).

As the skilled person will understand, the antibody of the invention will comprise a number of antigen binding sites. Framework sequences of the amino acid sequences of the selected $V_H$ and $V_L$ domains together with CDR sequences are combined in an antigen binding site. Specific combinations of framework sequences from $V_H$ and $V_L$ domains envisaged by the present invention are as presented in Table 3 below, wherein an "X" is presented at a position of a combination of a $V_H$ and $V_L$ domain envisaged.

TABLE 3

$V_H$ and $V_L$ combination of framework sequences.

| | | $V_H$ SEQ ID NO | | | | | | | |
|---|---|---|---|---|---|---|---|---|---|
| | | 12 | 14 | 16 | 18 | 32 | 34 | 36 | 38 | 40 |
| $V_L$ SEQ ID NO. | 30 | X | X | X | <u>X</u> | <u>X</u> | <u>X</u> | <u>X</u> | <u>X</u> | <u>X</u> |

The combination of framework sequences from these $V_H$ and $V_L$ domains results in antibodies having functional binding to human APRIL. It should be noted, as is further presented in the experimental section, that in the tests performed by the inventors of the present invention, antibodies having APRIL binding functionality were only obtained, when combining the $V_H$ sequences of the invention with the $V_L$ sequence of SEQ ID NO: 30 (VL15). In the tested combinations of the selected $V_H$ sequences with other $V_L$ sequences (VL10-VL14), the obtained antibodies did not have functional APRIL binding properties. A further surprising effect of the combination of the $V_H$ and $V_L$ sequences used in accordance with the present invention is an improved (thermo)stability in comparison to antibodies having the hAPRIL.01A $V_H$ and $V_L$ sequences as is presented in the experimental section.

There is a preference for combining the VL framework sequences of SEQ ID NO: 30 with the VH framework sequences from the VH framework sequences of SEQ ID NO: 18 or sequences derived therefrom, such as SEQ ID NO 32, 34, 36, 38, 40. These preferred combinations are presented with an underlined "X" in Table 3. The most preferred combination of VL framework sequences from SEQ ID NO: 30 with VH framework sequences from SEQ ID NO: 40 is presented in table 3 as an "X" in bold (and underlined) font. It has been surprisingly found that these combinations of VL and VH framework sequences result in antibodies having additional beneficial features, including beneficial stability features and/or improved binding to the human APRIL target.

According to certain embodiments in the $V_H$ domain at least one of CDR1, CDR2, CDR3 is selected from the group consisting of respectively SEQ NO 5, 6, 7, or a variant of any of said sequences. Preferably in the $V_H$ domain, CDR1, CDR2 and CDR3 are selected from respectively SEQ NO 5, 6, 7, or a variant of any of said sequences. These $V_H$ domain CDR sequences correspond to the $V_H$ domain CDRs of hAPRIL.01A.

According to certain embodiments in the $V_L$ domain at least one of CDR1, CDR2, CDR3 is selected from the group consisting of respectively SEQ NO 8, 9, 10, or a variant of any of said sequences. Preferably in the $V_L$ domain CDR1, CDR2 and CDR3 are selected from respectively SEQ NO 8, 9, 10, or a variant of any of said sequences. These $V_L$ domain CDR sequences correspond to the $V_L$ domain CDRs of hAPRIL.01A.

According to certain embodiments in an antigen binding site of the antibody the $V_H$ domain CDR1, CDR2 and CDR3 are selected from respectively SEQ NO 5, 6, 7, or a variant of any of said sequences and the $V_L$ domain CDR1, CDR2 and CDR3 of are selected from respectively SEQ NO 8, 9, 10, or a variant of any of said sequences.

The inventors of the present invention have surprisingly found that further improvements can be made in the antibodies combining the VH and VL framework sequences used in the present invention. In particular the substitution R72S in the VH amino acid sequence results in improved binding to human APRIL.

In addition the combined substitution R67K-V68A in the VH amino acid sequence also results in improved binding to human APRIL. The invention therefore according to certain embodiments relates to antibodies wherein in the VH amino acid sequence the amino acid at position 72 is S. The VH amino sequences of SEQ ID NO. 32, 34, 36, 38, 40 are examples of such VH amino acid sequences having an S residue at position 72. According to other embodiments the invention relates to antibodies wherein in the VH amino acid sequence the amino acid at position 67 is K and the amino acid at position 68 is A. The combination of all three amino acid substitutions R72S, R67K and V68A is also envisaged within the present invention. Thus according to other embodiments the invention relates to antibodies wherein in the $V_H$ amino acid sequence the amino acid at position 72 is S, the amino acid at position 67 is K and the amino acid at position 68 is A.

Apart from $V_H$ and $V_L$ domains, the antibody may comprise additional domains such as a suitable number of $C_H$ domains and a suitable number of $C_L$ domains. $C_H$ domains and $C_L$ domains may be of human origin. Such domains also include domains that provide antibodies with modified (or blocked) Fc regions to provide altered effector functions. See, e.g. U.S. Pat. No. 5,624,821; WO2003/086310; WO2005/120571; WO2006/0057702; Presta, 2006, *Adv. Drug Delivery Rev.* 58:640-656; Vincent and Zurini, *Biotechnol. J.*, 2012, 7:1444-50; Kaneko and Niwa, *Biodrugs*, 2011, 25: 1-11. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. According to certain embodiments it is preferred to use Fc regions displaying reduced Fc effector functions. The antibodies of the present invention according to certain embodiments may also have Fc regions originating from human IgG4 and/or Fc regions carrying a N297Q glycosylation deficient mutant. $C_L$ domains may be selected from human Kappa or Lamba constant domains. Preferably, human Kappa $C_L$ domain is used.

According to certain embodiments of the invention, antibodies comprising Fc and $C_L$ domains are provided, wherein the $V_H$ domain amino acid sequence is in a heavy chain amino acid sequence having at least 70% sequence similarity with an amino acid sequence selected from SEQ ID NO: 42, 44, 46, 48, 52 preferably SEQ ID NO: 48 or 52, most preferably SEQ ID NO: 52, and the $V_L$ domain amino acid sequence is in a light chain amino acid sequence having at least 70% sequence similarity with an amino acid sequence selected from SEQ ID NO: 50.

Specific combinations of these heavy and light chains envisaged by the present invention are as presented in Table 4 below, wherein an "X" is presented at a position of a combination of a heavy and light chain envisaged.

TABLE 4

| | | Heavy chain SEQ ID NO | | | | |
|---|---|---|---|---|---|---|
| | | 42 | 44 | 46 | 48 | 52 |
| Light chain SEQ ID NO. | 50 | X | X | X | <u>X</u> | <u>X</u> |

Preferred combinations are indicated with an underlined "X" in. More preferred combinations are indicated with an "X" in bold (and underlined) font.

According to a further aspect, the invention relates to an isolated polynucleotide encoding a $V_H$ domain and/or a $V_L$ domain of an antibody according to the invention. A polynucleotide sequence encoding the $V_H$ domain preferably is a polynucleotide sequence having at least 70% sequence similarity with a polynucleotide sequence selected from SEQ ID NO: 11, 13, 15, 17, 31, 39, 41, 43, 45, 47, 51 preferably SEQ ID NO: 17, 31, 39, 47 or 51, more preferably SEQ ID NO: 51. A polynucleotide sequence encoding the $V_L$ domain preferably is a polynucleotide sequence having at least 70% sequence similarity with a polynucleotide sequence selected from SEQ ID NO: 29 or 49, preferably SEQ ID NO: 49.

The invention further relates to an expression unit comprising a number of expression vectors, comprising a number of polynucleotides according to the invention under the control of suitable regulatory sequences, wherein the number of polynucleotides encode the $V_H$ domain and the $V_L$ domain of an antibody according to the invention. The expression unit may be designed such that the polynucleotide sequence coding for the $V_H$ domain and the polynucleotide sequence coding for $V_L$ domain may be on the same expression vector. Thus the expression unit may comprise a single vector. Alternatively the polynucleotide sequence coding for the $V_H$ domain and the polynucleotide sequence coding for the $V_L$ domain may be on different expression vectors. In such embodiments the expression unit will comprise a plurality, such as for example 2, expression vectors.

A further aspect of the invention relates to a host cell comprising a number of polynucleotides of the invention and/or an expression unit of the invention. The expression unit preferably is an expression unit comprising an expression vector comprising both a polynucleotide sequence coding for the $V_H$ domain and a polynucleotide sequence coding for the $V_L$ domain.

The antibody of the invention can be any one of the following:
- a chimeric antibody or a fragment thereof;
- a humanized antibody or a fragment thereof; or
- an antibody fragment selected from the group consisting of Fab, Fab', Fab'-SH, Fv, scFv, F(ab')$_2$, bispecific mAb and a diabody. Humanized antibodies comprising a number of antigen binding sites based on the CDRs of hAPRIL.01A are preferred. It may be noted that the framework regions selected according to the invention are from human origin and thus may be suitably used for obtaining humanized antibodies, in particular when combined with constant regions from human origin.

According to a further aspect thereof, the invention relates to a method of producing an antibody of the invention, which method comprises:
a) culturing a host cell comprising a number of polynucleotides of the invention and/or an expression unit of the invention in culture medium under conditions wherein the polynucleotide is expressed, thereby producing polypeptides comprising the light and heavy chain variable regions; and
b) recovering the polypeptides from the host cell or culture medium.

The invention further relates to a composition comprising an antibody of the invention in combination with a pharmaceutically acceptable carrier or diluent. Such composition in one embodiment may comprise more than one antibody. In one embodiment, the composition comprises one or more other active compounds in addition to the one or more antibodies of the invention. Such combination compositions can be used for combination therapy, for example in the treatment of cancer. In that case the antibody may be combined with one or more of the usual anticancer drugs. For other combination therapies other additional active compounds may be used. For combination therapy it is not obligatory to have the two or more active compounds in the same composition. Thus, also part of the invention is the combined or subsequent use of the antibodies and the other active compound, wherein the antibody and the other active compound are administered simultaneously or subsequently.

As is clear from the description above, the antibody of the invention may be for use in therapy and diagnosis and for other, non-therapeutic purposes. The invention thus further relates to methods of use of the antibodies in therapy and diagnosis and for other, non-therapeutic purposes.

In one embodiment, the therapy comprises inhibition of immune cell proliferation and/or immune cell survival. In another embodiment the treatment is aimed at treating cancer. In one embodiment, the therapy comprises the treatment of an autoimmune disease. In one embodiment, the therapy comprises the treatment of an inflammatory disease. In one embodiment, the therapy comprises the treatment of an Ig secretion mediated disease, in particular an IgA secretion mediated disease. The therapeutic uses of the antibody of the invention will be discussed in more detail below.

The antibody of the invention when used in non-therapeutic applications can for example be applied in in vitro or ex vivo techniques, such as flow-cytometry, Western blotting, enzyme-linked immunosorbent assay (ELISA) and immunohistochemistry.

Therapy

In view of the fact that the antibodies of the present invention bind to human APRIL analogous to hAPRIL.01A, the antibodies of the present invention are suitable for use in therapy analogous to hAPRIL.01A, with the improvements discussed above and in the experimental section. Therefore, the antibodies of the present invention are suitable for treatment of a condition known or expected to be ameliorated by blocking the interaction of human APRIL with BCMA and/or TACI. As is already known in the art, blocking the interaction of human APRIL with BCMA and/or TACI inhibits immune cell proliferation and/or survival and thus may be of value for the treatment of conditions where such blocking of immune cell proliferation and/or survival is beneficial, such as inflammatory diseases, diseases mediated by Ig secretion and/or autoimmune diseases. Blocking of the interaction of human APRIL with BCMA and/or TACI may also be beneficial in the treatment of cancer.

Autoimmune conditions for which an antibody of the invention may be beneficial may be selected from multiple sclerosis, rheumatoid arthritis, type 1 diabetes, psoriasis, Crohn's disease and other inflammatory bowel diseases such as ulcerative colitis, systemic lupus eythematosus (SLE), autoimmune encephalomyelitis, myasthenia gravis (MG), Hashimoto's thyroiditis, Goodpasture's syndrome, pemphigus, Graves disease, autoimmune hemolytic anemia, autoimmune thrombocytopenic purpura, scleroderma with anticollagen antibodies, mixed connective tissue disease, polypyositis, pernicious anemia, idiopathic Addison's disease, autoimmune associated infertility, glomerulonephritis, crescentic glomerulonephritis, proliferative glomerulonephritis, bullous pemphigoid, Sjogren's syndrome, psoriatic arthritis, insulin resistance, autoimmune diabetes mellitus, autoimmune hepatitis, autoimmune hemophilia, autoimmune lymphoproliferative syndrome (ALPS), autoimmune hepatitis, autoimmune hemophilia, autoimmune lymphoproliferative syndrome, autoimmune uveoretinitis, Guillain-Bare syndrome, arteriosclerosis and Alzheimer's disease.

In addition, the antibodies of the invention may also be beneficial in the treatment of other conditions associated where lowering of immune responses is beneficial, such as graft (transplant) rejection or allergic conditions.

Also, the antibodies of the invention may be beneficial in the treatment of other conditions wherein lowering of Immunoglobulin levels, such as IgA, including IgA1 or IgA2, IgG, IgM levels, is beneficial, such as conditions associated with Ig secretion, in particular IgA secretion, Ig overproduction, such as IgA, including IgA1 or IgA2, IgG, IgM over production, in particular IgA overproduction, or Ig deposition, in particular IgA deposition. Examples of such conditions include, but are not limited to IgA nephropathy and other forms of glomerulonephritis, celiac disease, pemphigoid diseases, Henloch-Schönlein purpura, and other autoimmune diseases that are associated with Ig deposition.

Within the present invention the treatment of the "condition" includes any therapeutic use including prophylactic and curative uses of the anti-human APRIL antibody. Therefore the term "condition" may refer to disease states but also to physiological states in the prophylactic setting where physiology is not altered to a detrimental state.

Cancers within the present invention include, but are not limited to, leukemia, acute lymphocytic leukemia, acute myelocytic leukemia, myeloblasts promyelocyte, myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system. Cancers that are of particular interest are cancers having cells expressing APRIL, such as B-cell derived malignancies, lymphoid or colon or lung carcinoma's or multiple myeloma (MM) or Chronic Lymphocytic Leukaemia (CLL) B cells.

For the purpose of treatment of any of the conditions mentioned above, the antibody of the invention can be dosed directly to subjects, alone or in combination with other therapeutic agents. Therefore, according to certain embodiments of the invention an antibody of the invention in its use and/or in a composition may be combined with a number of chemotherapeutic agents, which are used to treat multiple myeloma (MM), Myelodysplastic syndrome (MDS), Waldenstroms macroglobinemia, B-CLL, Diffuse large cell B cell lymphoma, Non-Hodgkin Lymphoma and wegeners granulomatosis, such as melphalan, vincristine, fludarabine, chlorambucil, bendamustine, etoposide, doxorubicin, cyclophosphamide, cisplatin. In addition, an antibody of the invention in its use and/or in a composition may be combined with a number of immune modulating agents such as corticosteroids (dexamethasone, prednisolone), thalidomide analogs (thalidomide, lenalidomide, pomalidomide). Also an antibody of the invention in its use and/or in a composition may be combined with a number of targeted kinase inhibitors, such as ibrutinib, idelalisib. Furthermore, an antibody of the invention in its use and/or in a composition may be combined with a number of antibody therapies targeting CD20, such as rituximab, ofatumumab, obinotuzumab; or antibody therapies targeting CD52 such as alemtuzumab; or antibody therapies targeting CD38 such as daratumumab; or antibody therapies targeting IL-6 or IL-6 receptor (such as sarilumab, tocilizumab); or antibody therapies targeting CS-1 (such as elotuzumab); or antibody therapies targeting BCMA (such as GSK2857916); or antibody therapies targeting BAFF or BLyss (such as tabalumab). In addition, an antibody of the invention in its use and/or in a composition may be combined with a number bisphosphonates (such as pamidronate, zolendronic acid). It is described previously that APRIL protects MM cells from IL-6 deprivation, dexamethasone and bortezomib treatment (Moreaux et al, 2004, *Blood* 103(8): 3148-57; Li et al., 2010, *Med Oncol.* 27:439-45). hAPRIL.01A has been shown to reverse the APRIL mediated survival of MM cells in lenalidomide and dexamethasone treatment (Tai et al., 2014, ASH poster 2098). In view of these findings in the art, the antibody of the present invention may in particular be combined in its use and/or in a composition with a further therapeutic agent selected from corticosteroids, for example dexamethasone, prednisolone, preferably dexamethasone, or thalidomide analogs, for example thalidomide, lenalidomide, pomalidomide, in particular lenalidomide, or with bortezomid.

Diagnosis

With APRIL representing an important marker for diseases, such as, but not limited to autoimmune diseases, inflammatory diseases and malignancies, detection of APRIL in the serum and/or tissue of human subjects is important. For diagnostic applications, the antibodies typically will be labeled (either directly or indirectly) with a detectable moiety. Numerous labels are available which can be generally grouped into the following categories: biotin, fluorochromes, radionucleotides, enzymes, iodine, and biosynthetic labels.

Soluble APRIL present in the serum and other body fluids and/or tissue of a range of different patients has been shown to correlate with disease severity of the patients. For example, patients suffering from chronic lymphocytic leukemia (CLL), Hodgkin's lymphoma, Non-Hodgkin's lymphoma (NHL) and Multiple Myeloma (MM), DLBCL patients (NHL), colorectal cancer, SLE, a wider range of systemic immune-based rheumatic diseases (now also including Sjögren's syndrome, Reiter's syndrome, psoriatic arthritis, polymyositis, and ankylosing spondylitis) and atopic dermatitis demonstrated increased serum levels of soluble APRIL. In addition, serum APRIL levels in patients suffering from IgA nephropathy are elevated (McCarthy et al., 2011, *J. Clin. Invest.* 121(10):3991-4002). Also, serum APRIL levels are elevated in sepsis and predict mortality in critically ill patients (Jonsson et al., 1986, *Scand J Rheumatol Suppl* 61, 166-9; Roschke et al., 2002, *J Immunol* 169, 4314-21). Based on the demonstrated binding characteristics of hAPRIL.01A, antibodies according to the invention can be used as a diagnostic tool to detect soluble APRIL in the body fluids and/or tissue.

The antibodies of the present invention may be employed in any known assay method, such as competitive binding assays, direct and indirect sandwich assays, and immunoprecipitation assays. Zola, Monoclonal Antibodies. A Manual of Techniques, pp. 147-158 (CRC Press, Inc. 1987).

The antibodies of the invention may also be used for in vivo diagnostic assays. Generally, the antibody is labeled with a radionuclide so that the antigen or cells expressing it can be localized using immunoscintigraphy or positron emission tomography.

Non-Therapeutic Uses

According to another aspect of the invention, the antibodies have other, non-therapeutic uses. The non-therapeutic uses for the antibodies of the invention include flow cytometry, western blotting, enzyme linked immunosorbant assay (ELISA) and immunohistochemistry.

The antibodies of this invention may for example be used as an affinity purification reagent via immobilization to a Protein A-Sepharose column.

GENERAL DEFINITIONS

The term "antibody" refers to any form of antibody that exhibits the desired biological activity, such as inhibiting binding of a ligand to its receptor, or by inhibiting ligand-induced signaling of a receptor. In the present case the biological activity comprises blocking of the binding of APRIL to its receptors BCMA and/or TACI. Thus, "antibody" is used in the broadest sense and specifically covers, but is not limited to, monoclonal antibodies (including full length monoclonal antibodies) and multispecific antibodies (e.g., bispecific antibodies) such as based on the Duobody® technology (Genmab) or Hexabody® technology (Genmab) or antibody fragment.

"Antibody fragment" and "antibody binding fragment" mean antigen-binding fragments and analogues of an antibody, typically including at least a portion of the antigen binding or variable regions (e.g. one or more CDRs) of the parental antibody. An antibody fragment retains at least some of the binding specificity of the parental antibody. Typically, an antibody fragment retains at least 10% of the parental binding activity when that activity is expressed on a molar basis. Preferably, an antibody fragment retains at least 20%, 50%, 70%, 80%, 90%, 95% or 100% or more of the parental antibody's binding affinity for the target. Examples of antibody fragments include, but are not limited to, Fab, Fab', F(ab')2, and Fv fragments; diabodies; linear antibodies; single-chain antibody molecules, e.g., sc-Fv, unibodies (technology from Genmab); nanobodies (technology from Ablynx); domain antibodies (technology from Domantis); and multispecific antibodies formed from antibody fragments. Engineered antibody variants are reviewed in Holliger and Hudson, 2005, Nat. Biotechnol. 23:1126-1136.

An "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

An "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')2 molecule.

An "F(ab')2 fragment" contains two light chains and two heavy chains containing a portion of the constant region between the $C_H1$ and $C_H2$ domains, such that an interchain disulfide bond is formed between the two heavy chains. A F(ab')2 fragment thus is composed of two Fab' fragments that are held together by a disulfide bond between the two heavy chains.

The "Fv region" comprises the variable regions from both the heavy and light chains, but lacks the constant regions.

A "single-chain Fv antibody" (or "scFv antibody") refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun, 1994, The Pharmacology of Monoclonal Antibodies, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "diabody" is a small antibody fragment with two antigen-binding sites. The fragments comprises a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al., 1993, Proc. Natl. Acad. Sci. USA 90: 6444-6448.

"Duobodies" are bispecific antibodies with normal IgG structures (Labrijn et al., 2013, Proc. Natl. Acad. Sci. USA 110 (13): 5145-5150).

"Hexabodies" are antibodies that while retaining regular structure and specificity have an increased killing ability (Diebolder et al., 2014, Science 343(6176):1260-3).

A "domain antibody fragment" is an immunologically functional immunoglobulin fragment containing only the variable region of a heavy chain or the variable region of a light chain. In some instances, two or more $V_H$ regions are covalently joined with a peptide linker to create a bivalent domain antibody fragment. The two $V_H$ regions of a bivalent domain antibody fragment may target the same or different antigens.

As used herein antibody hAPRIL.01A is a mouse antibody wherein the heavy chain has the amino acid sequence of SEQ ID NO: 55 and the light chain has the amino acid sequence of SEQ ID NO: 56.

An antibody fragment of the invention may comprise a sufficient portion of the constant region to permit dimerization (or multimerization) of heavy chains that have reduced disulfide linkage capability, for example where at least one of the hinge cysteines normally involved in inter-heavy chain disulfide linkage is altered as described herein. In another embodiment, an antibody fragment, for example one that comprises the Fc region, retains at least one of the biological functions normally associated with the Fc region when present in an intact antibody, such as FcRn binding, antibody half life modulation, ADCC (antibody dependent cellular cytotoxicity) function, and/or complement binding (for example, where the antibody has a glycosylation profile necessary for ADCC function or complement binding).

The term "chimeric" antibody refers to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (See, for example, U.S. Pat. No. 4,816,567 and Morrison et al., 1984, Proc. Natl. Acad. Sci. USA 81:6851-6855).

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The humanized forms of rodent antibodies will essentially comprise the same CDR sequences of the parental rodent antibodies, although certain amino acid substitutions may be included to increase affinity, increase stability of the humanized antibody, or for other reasons.

The antibodies of the present invention also include antibodies with modified (or blocked) Fc regions to provide altered effector functions. See, e.g. U.S. Pat. No. 5,624,821; WO2003/086310; WO2005/120571; WO2006/0057702; Presta, 2006, Adv. Drug Delivery Rev. 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta, 2005, J. Allergy Clin. Immunol. 116:731 at 734-35.

The antibodies of the present invention also include antibodies with intact Fc regions that provide full effector functions, e.g. antibodies of isotype IgG1, which induce complement-dependent cytotoxicity (CDC) or antibody dependent cellular cytotoxicity (ADCC) in the a targeted cell.

The antibodies may also be conjugated (e.g., covalently linked) to molecules that improve stability of the antibody during storage or increase the half-life of the antibody in vivo. Examples of molecules that increase the half-life are albumin (e.g., human serum albumin) and polyethylene glycol (PEG). Albumin-linked and PEGylated derivatives of antibodies can be prepared using techniques well known in the art. See, e.g. Chapman, 2002, Adv. Drug Deliv. Rev. 54:531-545; Anderson and Tomasi, 1988, J. Immunol. Methods 109:37-42; Suzuki et al., 1984, Biochim. Biophys. Acta 788:248-255; and Brekke and Sandlie, 2003, Nature Rev. 2:52-62.

The term "hypervariable region," as used herein, refers to the amino acid residues of an antibody which are responsible for antigen-binding. The hypervariable region comprises amino acid residues from a "complementarity determining region" or "CDR," defined by sequence alignment, for example residues 24-34 (L1), 50-56 (L2) and 89-97 (L3) in the light chain variable domain and 31-35 (H1), 50-65 (H2) and 95-102 (H3) in the heavy chain variable domain (see Kabat et al., 1991, Sequences of proteins of Immunological Interest, 5th Ed. Public Health Service, National Institutes of Health, Bethesda, Md.) and/or those residues from a "hypervariable loop" (HVL), as defined structurally, for example, residues 26-32 (L1), 50-52 (L2) and 91-96 (L3) in the light chain variable domain and 26-32 (H1), 53-55 (H2) and 96-101 (H3) in the heavy chain variable domain (see Chothia and Leskl, 1987, J. Mol. Biol. 196:901-917).

"Framework" or "FR" residues or sequences are those variable domain residues or sequences other than the CDR residues as herein defined.

The antibody of the invention according to certain embodiments may be an isolated antibody. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "monoclonal antibody" when used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975, *Nature* 256:495, or may be made by recombinant DNA methods (see, for example, U.S. Pat. No. 4,816,567). The "monoclonal antibodies" may also be isolated from phage antibody libraries using the techniques described in Clackson et al., 1991, *Nature* 352:624-628 and Marks et al., 1991, *J. Mol. Biol.* 222:581-597, for example. The monoclonal antibodies herein specifically include "chimeric" antibodies.

As used herein, the term "immune cell" includes cells that are of hematopoietic origin and that play a role in the immune response. Immune cells include lymphocytes, such as B cells and T cells, natural killer cells, myeloid cells, such as monocytes, macrophages, eosinophils, mast cells, basophils, and granulocytes.

As used herein, an "immunoconjugate" refers to an anti-human APRIL antibody, or a fragment thereof, conjugated to a therapeutic moiety, such as a bacterial toxin, a cytotoxic drug or a radiotoxin. Toxic moieties can be conjugated to antibodies of the invention using methods available in the art.

As used herein, a sequence "variant" or "variant sequence" refers to a sequence that differs from the disclosed sequence at one or more amino acid residues but which retains the biological activity of the parent molecule. The invention includes the variants of antibodies explicitly disclosed by the various sequences. For the $V_H$ domain CDR1, CDR2 and CDR3 sequences, according to some embodiments, variant sequences may comprise up to 6 amino acid substitutions, such as 1, 2, 3, 4, 5 or 6 amino acid substitutions, for the CDR1, CDR2 and CDR3 sequences taken together. Similarly for the $V_L$ domain CDR1, CDR2 and CDR3 sequences, according to some embodiments, variant sequences may comprise up to 6 amino acid substitutions, such as 1, 2, 3, 4, 5 or 6 amino acid substitutions, for the CDR1, CDR2 and CDR3 sequences taken together.

"Conservatively modified variants" or "conservative amino acid substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, The Benjamin/Cummings Pub. Co., p. 224 (4th Edition 1987)). Such exemplary substitutions are preferably made in accordance with those set forth above in Table 2.

As used herein, the term "about" refers to a value that is within an acceptable error range for the particular value as determined by one of ordinary skill in the art, which will depend in part on how the value is measured or determined, i.e. the limitations of the measurement system. For example, "about" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

The term "a number of" should be understood as meaning one or more. Depending on the context of its use "a number of" may refer to any suitable number selected from 1, 2, 3, 4, 5, 6, 7, 8, 9, 10. According to certain embodiments "a number of" may have the meaning of "a plurality". Depending on the context of its use "a plurality" may refer to any suitable number selected from 2, 3, 4, 5, 6, 7 8, 9, 10.

"Specifically" binds, when referring to a ligand/receptor, antibody/antigen, or other binding pair, indicates a binding reaction which is determinative of the presence of the protein, e.g., APRIL, in a heterogeneous population of proteins and/or other biologics. Thus, under designated conditions, a specified ligand/antigen binds to a particular receptor/antibody and does not bind in a significant amount to other proteins present in the sample.

"Administration", "therapy" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration", "therapy" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration", "therapy" and "treatment" also mean in vitro and ex vivo treatments, e.g., of a cell, by a reagent, diagnostic, binding composition, or by another cell. Within the present description of the invention the terms "in vitro" and "ex vivo" have a similar meaning and may be used interchangeably.

The antibody DNA also may be modified, for example, by substituting the coding sequence for human heavy- and light-chain constant domains in place of the homologous murine sequences (U.S. Pat. No. 4,816,567; Morrison, et al., 1984, *Proc. Natl Acad. Sci. USA*, 81:6851), or by covalently joining to the immunoglobulin coding sequence all or part of the coding sequence for non-immunoglobulin material (e.g., protein domains). Typically such non-immunoglobulin material is substituted for the constant domains of an antibody, or is substituted for the variable domains of one antigen-combining site of an antibody to create a chimeric bivalent antibody comprising one antigen-combining site having specificity for an antigen and another antigen-combining site having specificity for a different antigen.

Amino acid sequence variants of the anti-human APRIL antibodies of the invention are prepared by introducing appropriate nucleotide changes into the coding DNAs, or by peptide synthesis. Such variants include, for example, deletions from, and/or insertions into, and/or substitutions of, residues within the amino acid sequences shown for the anti-APRIL antibodies. Any combination of deletion, insertion, and substitution is made to arrive at the final construct, provided that the final construct possesses the desired characteristics. The amino acid changes also may alter post-translational processes of the anti-APRIL antibodies, such as changing the number or position of glycosylation sites.

A useful method for identification of certain residues or regions of the anti-APRIL antibodies polypeptides that are preferred locations for mutagenesis is called "alanine scanning mutagenesis," as described by Cunningham and Wells, 1989, *Science* 244: 1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with APRIL antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed anti-APRIL antibodies' variants are screened for the desired activity.

Ordinarily, amino acid sequence variants of the anti-APRIL antibodies will have an amino acid sequence having at least 75% amino acid sequence similarity with the original antibody amino acid sequences of either the heavy or the light chain more preferably at least 80%, more preferably at least 85%, more preferably at least 90%, and most preferably at least 95%, 98% or 99%. Similarity or homology with respect to this sequence is as defined above.

Antibodies having the characteristics identified herein as being desirable can be screened for increased biologic activity in vitro or suitable binding affinity. To screen for antibodies that bind to the same epitope on human APRIL as hAPRIL.01A, a routine cross-blocking assay such as that described in Antibodies, A Laboratory Manual, Cold Spring Harbor Laboratory, Ed Harlow and David Lane (1988), can be performed. Antibodies that bind to the same epitope are likely to cross-block in such assays, but not all cross-blocking antibodies will necessarily bind at precisely the same epitope since cross-blocking may result from steric hindrance of antibody binding by antibodies bind at overlapping epitopes, or even nearby non-overlapping epitopes.

Alternatively, epitope mapping, e.g., as described in Champe et al., 1995, *J. Biol. Chem.* 270:1388-1394, can be performed to determine whether the antibody binds an epitope of interest. "Alanine scanning mutagenesis," as described by Cunningham and Wells, 1989, *Science* 244: 1081-1085, or some other form of point mutagenesis of amino acid residues in human APRIL may also be used to determine the functional epitope for anti-APRIL antibodies of the present invention.

Another method to map the epitope of an antibody is to study binding of the antibody to synthetic linear and CLIPS peptides that can be screened using credit-card format mini PEPSCAN cards as described by Slootstra et al. (Slootstra et al., 1996, *Mol. Diversity* 1: 87-96) and Timmerman et al. (Timmerman et al., 2007, *J. Mol. Recognit.* 20: 283-299). The binding of antibodies to each peptide is determined in a PEPSCAN-based enzyme-linked immuno assay (ELISA).

Additional antibodies binding to the same epitope as hAPRIL.01A may be obtained, for example, by screening of antibodies raised against APRIL for binding to the epitope, or by immunization of an animal with a peptide comprising a fragment of human APRIL comprising the epitope sequences. Antibodies that bind to the same functional epitope might be expected to exhibit similar biological activities, such as similar APRIL binding and BCMA and TACI blocking activity, and such activities can be confirmed by functional assays of the antibodies.

The antibody can be selected from any class of immunoglobulins, including IgM, IgG, IgD, IgA, and IgE. Preferably, the antibody is an IgG antibody. Any isotype of IgG can be used, including IgG1, IgG2, IgG3, and IgG4. Variants of the IgG isotypes are also contemplated. The antibody may comprise sequences from more than one class or isotype. Optimization of the necessary constant domain sequences to generate the desired biologic activity is readily achieved by screening the antibodies in the biological assays described in the Examples.

Likewise, either class of light chain can be used in the compositions and methods herein. Specifically, kappa, lambda, or variants thereof are useful in the present compositions and methods.

The antibodies and antibody fragments of the invention may also be conjugated with cytotoxic payloads such as cytotoxic agents or radionucleotides such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$Cu, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe. Such antibody conjugates may be used in immunotherapy to selectively target and kill cells expressing a target (the antigen for that antibody) on their surface. Exemplary cytotoxic agents include ricin, *vinca* alkaloid, methotrexate, *Psuedomonas* exotoxin, saporin, diphtheria toxin, cisplatin, doxorubicin, abrin toxin, gelonin and pokeweed antiviral protein.

The antibodies and antibody fragments of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antibody molecules or protein molecules of the invention to the various moieties may be employed, including those methods described by Hunter et al., 1962, *Nature* 144:945; David et al., 1974, *Biochemistry* 13:1014; Pain et al., 1981, *J. Immunol. Meth.* 40:219; and Nygren, J., 1982, *Histochem. and Cytochem.* 30:407. Methods for conjugating antibodies and proteins are conventional and well known in the art.

Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., 1992, *Bio/Technology* 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the antibody. Protein A can be used to purify antibodies that are based on human Ig.gamma1, Ig.gamma2, or Ig.gamma4 heavy chains (Lindmark et al., 1983, *J. Immunol. Meth.* 62:1-13). Protein G is recommended for all mouse isotypes and for human .gamma.3 (Guss et al., 1986, *EMBO J* 5:1567-1575). The matrix to which the affinity ligand is attached is most often agarose, but other matrices are available.

Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In one embodiment, the glycoprotein may be purified using adsorption onto a lectin substrate (e.g. a lectin affinity column) to remove fucose-containing glycoprotein from the preparation and thereby enrich for fucose-free glycoprotein.

Pharmaceutical Formulations

The invention comprises pharmaceutical formulations of an anti-human APRIL antibody. To prepare pharmaceutical or sterile compositions, the antibody, in particular an antibody or fragment thereof, is admixed with a pharmaceutically acceptable carrier or excipient, see, e.g., Remington's Pharmaceutical Sciences and U.S. Pharmacopeia: National Formulary, Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al., 2001, *Goodman and Gilman's The Pharmacological Basis of Therapeutics*, McGraw-Hill, New York, N.Y.; Gennaro, 2000, Remington: *The Science and Practice of Pharmacy*, Lippincott, Williams, and Wilkins, New York, N.Y.; Avis, et al. (eds.), 1993, *Pharmaceutical Dosage Forms: Parenteral Medications*, Marcel Dekker, NY; Lieberman, et al. (eds.), 1990, *Pharmaceutical Dosage Forms: Tablets*, Marcel Dekker, NY; Lieberman, et al. (eds.), 1990, *Pharmaceutical Dosage Forms: Disperse Systems*, Marcel Dekker, NY; Weiner and Kotkoskie, 2000, *Excipient Toxicity and Safety*, Marcel Dekker, Inc., New York, N.Y.).

Toxicity and therapeutic efficacy of the antibody compositions, administered alone or in combination with another agent, such as the usual anti-cancer drugs, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

Suitable routes of administration include parenteral administration, such as intramuscular, intravenous, or subcutaneous administration and oral administration. Administration of antibodies, used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection. In one embodiment, the antibody of the invention is administered intravenously. In another embodiment, the antibody of the invention is administered subcutaneously.

Alternatively, one may administer the antibody in a local rather than systemic manner, for example, via injection of the antibody directly into the site of action, often in a depot or sustained release formulation. Furthermore, one may administer the antibody in a targeted drug delivery system.

Guidance in selecting appropriate doses of antibodies, cytokines, and small molecules are available (see, e.g., Wawrzynczak, 1996, *Antibody Therapy*, Bios Scientific Pub. Ltd, Oxfordshire, UK; Kresina (ed.), 1991, *Monoclonal Antibodies, Cytokines and Arthritis*, Marcel Dekker, New York, N.Y.; Bach (ed.), 1993, *Monoclonal Antibodies and Peptide Therapy in Autoimmune Diseases*, Marcel Dekker, New York, N.Y.; Baert, et al., 2003, *New Engl. J. Med.* 348:601-608; Milgrom, et al., 1999, *New Engl. J. Med.* 341:1966-1973; Slamon, et al., 2001, *New Engl. J. Med.* 344:783-792; Beniaminovitz, et al., 2000, *New Engl. J. Med.* 342:613-619; Ghosh, et al., 2003, *New Engl. J. Med.* 348:24-32; Lipsky, et al., 2000, *New Engl. J. Med.* 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

A preferred dose protocol is one involving the maximal dose or dose frequency that avoids significant undesirable side effects. A total weekly dose is generally at least 0.05 µg/kg body weight, more generally at least 0.2 µg/kg, most generally at least 0.5 µg/kg, typically at least 1 µg/kg, more typically at least 10 µg/kg, most typically at least 100 µg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al., 2003, *New Engl. J. Med.* 349:427-434; Herold, et al., 2002, *New Engl. J. Med.* 346:1692-1698; Liu, et al., 1999, *J. Neurol. Neurosurg. Psych.* 67:451-456; Portielji, et al., 2003, *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with disease and/or a reduction in the severity of such symptoms that will or are expected to develop with said disease. The terms further include ameliorating existing symptoms, preventing additional symptoms, and ameliorating or preventing the underlying causes of such symptoms. Thus, the terms denote that a beneficial result has been conferred on a vertebrate subject with a disease.

The antibody of the present invention for therapeutic purposes is administered in a therapeutically effective amount. As used herein, the term "therapeutically effective amount" or "effective amount" refers to an amount of an anti-APRIL antibody or fragment thereof, that when administered alone or in combination with an additional therapeutic agent to a cell, tissue, or subject is effective to prevent or ameliorate the disease or condition to be treated. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent are well known in the art, see, e.g., Hardman, et al. (eds.), 2001, *Goodman and Gilman's The Pharmacological Basis of Therapeutics*, 10th ed., McGraw-Hill, New York, N.Y.; Poole and Peterson (eds.), 2001, *Pharmacotherapeutics for Advanced Practice: A Practical Approach*, Lippincott, Williams & Wilkins, Phila., Pa.; Chabner and Longo (eds.), 2001, *Cancer Chemotherapy and Biotherapy*, Lippincott, Williams & Wilkins, Phila., Pa.

The pharmaceutical composition of the invention may also contain other agents, including but not limited to a cytotoxic, chemotherapeutic, cytostatic, anti-angiogenic or antimetabolite agents, a tumor targeted agent, an immune stimulating or immune modulating agent or an antibody conjugated to a cytotoxic, cytostatic, or otherwise toxic agent. The pharmaceutical composition can also be employed with other therapeutic modalities such as surgery, chemotherapy and radiation.

The invention will now be further illustrated and supported with reference to the following non-limiting experiments.

EXPERIMENTS

Experiment 1

Anti-APRIL Humanized Antibody Design
CDR Grafting

A unique antibody, hAPRIL.01A that binds human APRIL (WO2010/100056) was previously identified. The mouse hAPRIL.01A antibody was humanized by CDR-grafting technology (see e.g. U.S. Pat. No. 5,225,539 and Williams, D. G. et al., 2010, Antibody Engineering, volume 1, Chapter 21).

A strategy was designed in which first, human germline sequences were identified using IgBLAST (Ye J. et al., 2013, Nucleic Acids Res. 41:W34-40). For the hAPRIL.01A VH, human germline sequence IGHV1-3*01 (70.4% identity), and for the hAPRIL.01A VL, human germline sequence IGKV1-16*01 (65.3% identity) was identified.

Next, a database was constructed containing all human maturated sequences available in the IMGT database (release 201222-4: 161905 entries, indexed 4 Jun. 2012) (Lefranc, M.-P. et al., 1999, Nucleic Acid Res. 27:209-212) identifying 90,401 individual sequences. These sequences were queried using TBLASTN (2.2.26+) to identify template sequences that demonstrated the highest identify to hAPRIL.01A VH and VL sequences (SEQ IDs. 3 and 4, respectively). Three VH and seven VL sequences were selected that demonstrated a similarity score of 80% or higher and that displayed similar CDR lengths, preferably identical to those in hAPRIL.01A VH CDR1, CDR2, CDR3 (SEQ IDs. 5-7) and VL CDR1, CDR2 and CDR3 (SEQ IDs. 8-10), respectively.

For the heavy chain, the frameworks encoded by GenBank (Benson, D. A. et al., 2013, Nucleic Acids Res. 41(D1):D36-42) accession #AF022000, AB363149, and AB063827 were selected for straight grafting of the hAPRIL.01A VH CDRs, resulting in the following cDNA constructs: SEQ IDs. 11, 13, and 15, respectively. For the light chain, the frameworks encoded by GenBank accession #AX375917, DD272023, AB363267, AJ241396, DI152527, and DQ840975 were selected for straight grafting of the hAPRIL.01A VL CDRs, resulting in the following cDNA constructs: SEQ IDs. 19, 21, 23, 25, 27 and 29.

An additional heavy chain sequence was designed based on the consensus sequence from the alignment of the 25 best matching sequences (E-values 5e-46 to 9e-43) from the TBLASTN result, resulting in the following cDNA construct: SEQ ID 17.

To determine the structural effects of humanization of framework residues, a homology model of the hAPRIL.01A antibody was made using WHATIF (Krieger E. et al., 2003, Methods Biochem Anal. 44:509-23). The templates for the VH and VL chain, 2GKI (Kim Y. R. et al., 2006, J. Biol. Chem. 281: 15287-15295) and 2AEQ (Venkatramani L. et al. 2006, J. Mol. Biol. 356: 651-663) respectively were identified by a BLASTP search (Altschul, S. F. et al., 1990, J. Mol. Biol. 215:403-410) using the Protein Databank (www.rcsb.org, release June 2012; Berman H. M. et al., 2000, Nucleic Acids Res. 28:235-242). The VH and VL chains were combined as Fab fragment using a MUSTANG alignment (Konagurthu A. S. et al., 2006, Proteins 64:559-574), which was guided by the 2AEQ template. The constructed homology model of hAPRIL.01A was used to select residues that are affected by humanization and could affect the functionality of the humanized construct and the evaluation was made whether or not to replace selected residues:

for the sixth VL template (VL15) it was decided to replace VL residues Y49 and Y87 by smaller S49 and F87.

Signal Peptide Identification

Using NCBI IgBlast (BLASTN) (Ye J. et al., 2013, Nucleic Acids Res. 41 (Web Server issue):W34-40) human germline repertoire matching the mouse hAPRIL.01A VH and VL were identified and used to select the secretion leader for the VH and VL: VH, based on germline IGHV1-3*01 (NCBI accession #X62107), and VL, based on germline IGKV16*01 (NCBI accession #X62109). The following VH secretion leader sequence "MDWTWRILFLVAAAT-GAHS" (SEQ ID NO: 58) coded by SEQ ID NO: 57 and the VL secretion leader sequence "MDMRVLAQLLGLLLL-CFPGARC" (SEQ ID NO: 60) coded by SEQ ID NO: 59 were used to express all humanized VH and VL constructs.

An IgG4 version of humanized antibodies was produced, with the stabilizing Adair mutation (Angal S. et al., 1993, Mol Immunol. 30: 105-108), where Serine 241 (Kabat numbering) is converted to Proline.

Experiment 2

Synthesis, Subcloning, Expression, Binding

Synthesis cDNAs encoding humanized VH and VL constructs, SEQ IDs 11, 13, 15, 17, 21, 23, 25, 27, 29, were codon-optimized using OptGene software (version 2.0.6.0) and chemically synthesized by Baseclear. Next, sequences were cloned into the pUC57 vector (BaseClear), using a 5'-HindIII and 3'-ApaI (VH) or 3'-BsiWI (VL) restriction endonuclease cleavage site.

Subcloning

The humanized VH constructs were cloned into a pcDNA3.1(+) vector (Invitrogen) containing human IgG4 constant domains (CH1-CH3, GenBank accession #K01316) that had been cloned into EcoRI and HindIII restriction endonuclease cleavage sites, using the above-mentioned restriction endonuclease cleavage sites. The humanized VL constructs were cloned into a pcDNA3.1(+) vector (Invitrogen) containing a human CL (kappa) domain (GenBank accession #J00241) that had been cloned into HindIII and EcoRI restriction endonuclease cleavage sites, using the above-mentioned restriction endonuclease cleavage sites. Constructs were transformed in Subcloning efficient DH5α competent cells (Invitrogen) according to the manufacturer's instructions. Plasmid DNA was isolated using the Qiagen Plasmid Midi Kit (QIAGEN) according to manufacturer's protocol. The integrity of the constructs was confirmed by DNA sequencing (Macrogen).

Expression and Binding

The plasmids encoding the VH and VL constructs were mixed in a 1:3 ratio (4 μg in total) and transiently expressed by transfection into HEK293T human embryonic kidney cells (HEK293T/17, ATCC-CRL-11268), using Lipofectamine 2000 transfection reagent (Invitrogen) following the manufacturer's instructions. Cell supernatants were harvested after 5 days and tested for expression of antibody and binding to APRIL using an enzyme-linked immuno assay (ELISA). In these ELISAs, all incubation steps were followed by a wash step with PBST (PBS with 0.01% Tween 20). Maxisorb 96-wells plates (Nunc) were coated with 0.5 μg/ml anti-FLAG (Sigma) or anti-IgG4 (Jackson laboratories) and incubated overnight at 4° C. Subsequently the anti-FLAG coated 96-wells plates were incubated with FLAG-tagged human APRIL for 1 hour at room temperature. Next, supernatants and dilutions thereof were incubated for 1 hour, which was followed by an incubation of 1 hour with mouse anti-human IgG HRP-conjugate (Southern Biotechnology).

Immunoreactivity was visualized with 100 μl TMB Stabilized Chromagen (Invitrogen). Reactions were stopped with 100 μl 0.5 M H2504 and absorbances were measured at 450 and 620 nm.

Experiment 3

Purification and Stability

Purification

A subset of humanized antibodies described above was selected for further analyses. Again, plasmids encoding the VH and VL constructs were mixed in a 1:3 ratio (32 μg) and transiently expressed by transfection into ($8*10^6$) HEK293T human embryonic kidney cells (HEK293T), using Lipofectamine 2000 transfection reagent (Invitrogen) according to the manufacturer's instructions. Supernatants were harvested (10 ml) and antibodies were purified using MabSelect Sure Protein A resin according to the manufacturer's instructions (GE Healthcare). Buffer was exchanged for PBS using Zeba desalting columns (Thermo Scientific). The concentration of purified antibodies was determined based on OD280 (Nanodrop ND-1000). The binding of the purified antibodies to APRIL was established using the above described APRIL ELISA. The blocking capability of the humanized antibodies with BCMA and TACI receptors, was tested in a competition ELISA. In these ELISAs, all incubation steps were followed by a wash step with PBST (PBS with 0.01% Tween 20). Maxisorb 96-wells plates (Nunc) were coated with 0.5 μg/ml Fc-BCMA (R&D Systems) or Fc-TACI (R&D Systems) and incubated overnight at 4° C. Next, humanized antibodies and dilutions thereof were incubated, premixed with FLAG-tagged APRIL, for 1 hour, which was followed by an incubation of 1 hour with anti-FLAG HRP-conjugate (Sigma). Immunoreactivity was visualized with 100 μl TMB Stabilized Chromagen (Invitrogen). Reactions were stopped with 100 μl 0.5 M H2504 and absorbances were measured at 450 and 620 nm. Calculated $EC_{50}$ and $IC_{50}$ representing the concentration at which 50% of the total binding signal or blocking is observed are represented in Table 5.

TABLE 5

EC50 values, binding to APRIL. IC50, blockade of APRIL binding to BCMA-Fc. C4-hAPRIL.01A was used as experimental reference in each ELISA. n.c. indicates inhibition, but no IC50 could be calculated due to improper fitting.

| VH.VL combination | EC50 (nM) | IC50 (nM) |
|---|---|---|
| C4-hAPRIL.01A | 5.7 | 7.6 |
| VH11.VL15 | 120.8 | 4.3 |
| VH12.VL15 | 19.8 | n.c. |
| VH13.VL15 | 223.4 | n.c. |
| VH14.VL15 | 48.3 | n.c. |

For blockade of APRIL binding to TACI-Fc similar blocking effects were observed.

Surprisingly, combinations of VH11-VH14 with VL10-VL14 did not show nano- or micromolar EC50 values and only the combination of the selected VH framework sequences with framework sequences of VL15 resulted in antibodies having functional APRIL binding properties.

Stability

To determine the effect of humanization on the stability of the antibodies, humanized antibodies were exposed to a range of temperatures for 10 minutes. Purified antibodies were diluted to 3.16 µg/ml and dilutions thereof in PBS. Next, these solutions were exposed to 65° C. or 70° C. and residual binding after heat treatment of the antibodies was measured using the FLAG-tagged APRIL ELISA assay as described before (see Table 6).

TABLE 6

Residual binding of (humanized) antibodies to FLAG-APRIL as determined by ELISA. Binding is measured at three concentration: 3.16, 1 and 0.316 µg/ml. % Binding at 65 or 70° C. is expressed as % binding observed for each of the antibodies at Room Temperature (=100%).

|  |  | hAPRIL.01A | c4-hAPRIL.01A | 11.15 | 12.15 | 13.15 | 14.15 |
|---|---|---|---|---|---|---|---|
| | | | 65° C. | | | | |
| con- | 3.16 | 27.1 | 42.8 | 63.1 | 66.4 | 76.2 | 58.6 |
| cen- | 1 | 8.4 | 10.4 | 55.1 | 49.8 | 44.4 | 45.2 |
| tration | 0.316 | 13.7 | 18.8 | 74.6 | 74.3 | 66.1 | 63.7 |
| | | | 70° C. | | | | |
| Con- | 3.16 | 6.7 | 6.6 | 59.1 | 50.2 | 80.5 | 50.0 |
| cen- | 1 | 4.9 | 7.4 | 62.4 | 51.8 | 47.4 | 42.5 |
| tration | 0.316 | 11.2 | 16.9 | 82.0 | 70.3 | 65.0 | 63.1 |

Experiment 4

Improvement of Binding, Blocking and Stability by Back Mutations and Vernier Residues Improvement of Binding and Blockade by Back Mutations Analyses on sequence and structural level were performed to understand the molecular basis for the differences in binding and blockade of the different VH/VL combinations. A homology model of the humanized antibody was made, as described before. The template selected for both VH and VL was 3HC4 (Jordan J. L. et al., 2009, Proteins 77: 832-841). On the basis of careful analysis of the created model, the inventors of the present invention postulated that residue S72 in the selected VH chains is important for the orientation of the CDR2 loop. In order to investigate this postulation, mutation R72S was introduced in VH 14, which resulted in VH 14_1, SEQ ID 32 coded by the nucleotide sequence of SEQ ID 31. Antibody 14_1.15 was tested for binding and blockade as described before. As represented in Table 7, binding and blockade of antibody 14_1.15 are improved relative to the binding of antibody 14.15 as shown in table 5.

TABLE 7

Binding to APRIL and blockade of APRIL binding to BCMA-Fc of antibody 14_1.15. hAPRIL.01A and C4-hAPRIL.01A were used as experimental reference in each ELISA.

| VH.VL combination | EC50 (nM) | IC50 (nM) |
|---|---|---|
| VH14_1.VL15 | 1.29 ± 0.16 | 2.63 ± 0.55 |
| C4-hAPRIL.01A | 0.35 ± 0.13 | 0.77 ± 0.22 |
| hAPRIL.01A | 0.16 ± 0.14 | 0.46 ± 0.35 |

For blockade of APRIL binding to TACI-Fc similar IC50 values were obtained.

Vernier Residues

Analyses on sequence and structural level were performed to further improve binding and blockade of antibody 14_1.15. A homology model of this hAPRIL.01A analogue was made, as described before. The selected template for the VH chain was 2GKI and for the VL chain 4GMT (Lee P. S. et al., 2012, PNAS 109: 17040-17045), combined as a Fab fragment guided by template 2AEQ.

Residues close to the CDRs were studied in detail, since they could affect the loop conformation. In the analysis, the inventors identified a number of potentially relevant Vernier residues (Foote J. et al., 1992, J. Mol. Biol. 224:487-499). In order to evaluate their relevancy they were substituted with the mouse amino acid.

Introduction of mutation M70I resulted in VH14_1C (SEQ ID 33, 34) mutation T74K is present in VH14_1D (SEQ ID 35, 36), and mutation Q1E resulted in VH14_1E (SEQ ID 37, 38). The combined mutation of R67K and V68A resulted in VH 14_1G, SEQ ID 39, 40. The antibodies were tested for binding, blockade, and stability as described before. As represented in Table 8, surprisingly binding and blockade are improved with a factor 2 to 3. In particular the mutations introduced in antibody VH14_1G.VL15 surprisingly present a considerable improvement.

TABLE 8

Binding and blockade of antibody 14_1.15 and vernier zone mutants. hAPRIL.01A was used as experimental reference in each ELISA.

| VH.VL combination | EC50 (nM) | IC50 (nM) |
|---|---|---|
| VH14_1.VL15 | 1.29 ± 0.16 | 2.63 ± 0.55 |
| VH14_1C.VL15 | 7.04 ± 2.23 | 5.26 ± 0.08 |
| VH14_1D.VL15 | 1.95 ± 0.28 | 0.96 ± 0.38 |
| VH14_1E.VL15 | 2.67 ± 0.28 | 1.74 ± 0.32 |
| VH14_1G.VL15 | 0.78 ± 0.16 | 1.35 ± 0.39 |
| hAPRIL.01A | 0.16 ± 0.14 | 0.46 ± 0.35 |

In addition, the stability of the substituted humanized antibodies was improved as determined using thermostability studies as described in Example 3 (see Table 9).

TABLE 9

Residual binding of (humanized) antibodies to FLAG-APRIL as determined by ELISA. Binding is measured at three concentration: 3.16, 1 and 0.316 µg/ml. % Binding at 65 or 70° C. is expressed as % binding observed for each of the antibodies at Room Temperature (=100%).

|  |  | 14.15 | 14_1.15 | 14_1C.15 | 14_1D.15 | 14_1E.15 | 14_1G.15 |
|---|---|---|---|---|---|---|---|
| | | | | 65° C. | | | |
| concentration | 3.16 | 59.0 | 59.9 | 86.3 | 75.3 | 82.3 | 94.5 |
| | 1 | 47.5 | 46.1 | 44.7 | 39.8 | 39.7 | 31.3 |
| | 0.316 | 67.5 | 71.0 | 59.1 | 49.4 | 52.0 | 34.2 |

TABLE 9-continued

Residual binding of (humanized) antibodies to FLAG-APRIL as determined by ELISA.
Binding is measured at three concentration: 3.16, 1 and 0.316 µg/ml. % Binding at
65 or 70° C. is expressed as % binding observed for each of the antibodies
at Room Temperature (=100%).

|  |  | 14.15 | 14_1.15 | 14_1C.15 | 14_1D.15 | 14_1E.15 | 14_1G.15 |
|---|---|---|---|---|---|---|---|
|  |  |  | 70° C. |  |  |  |  |
| Concentration | 3.16 | 58.6 | 38.0 | 99.4 | 84.3 | 78.8 | 78.2 |
|  | 1 | 55.1 | 38.3 | 43.8 | 32.7 | 28.0 | 16.9 |
|  | 0.316 | 79.1 | 63.0 | 59.1 | 45.6 | 43.3 | 23.8 |

Experiment 5

14_1G.15 Demonstrates More Efficacious In Vivo Inhibition.

Figure 1B:
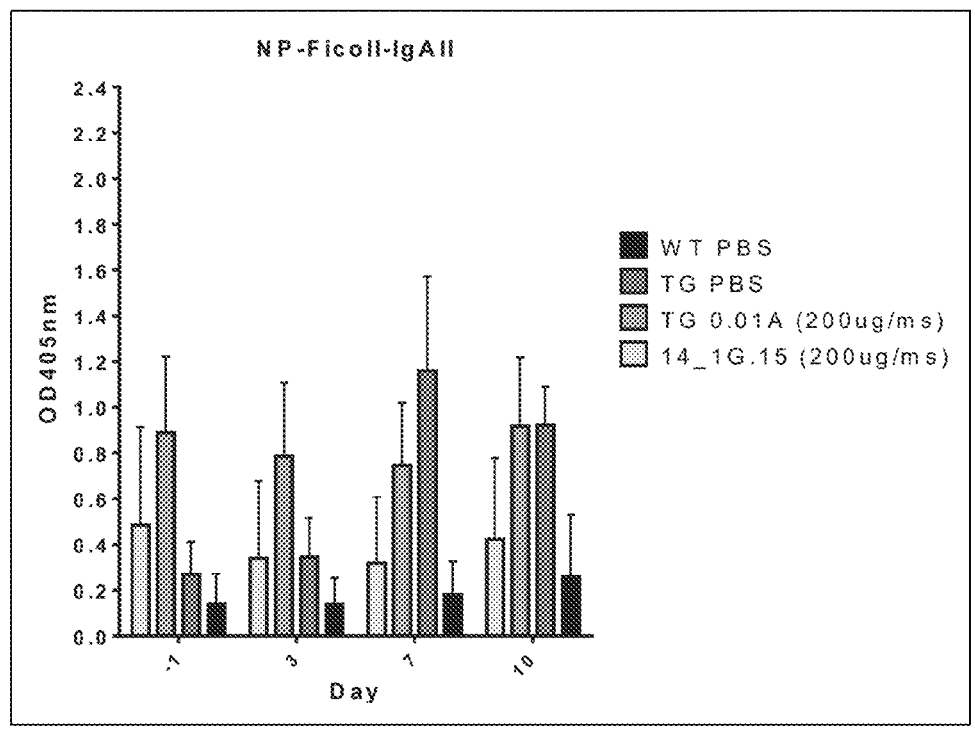
Figure 1C:
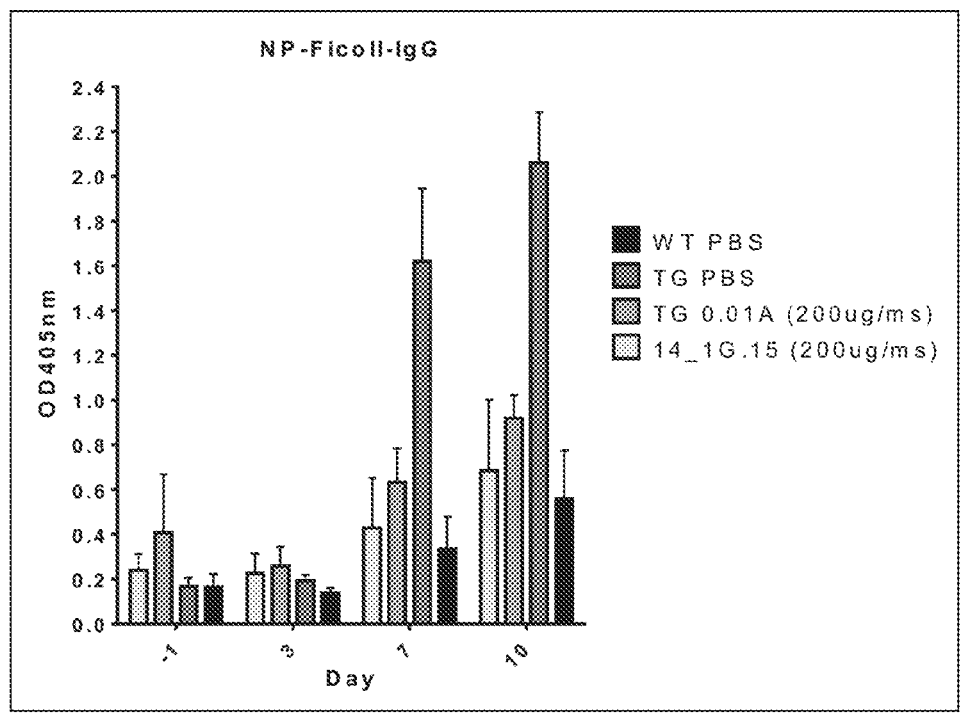
Figure 1D:
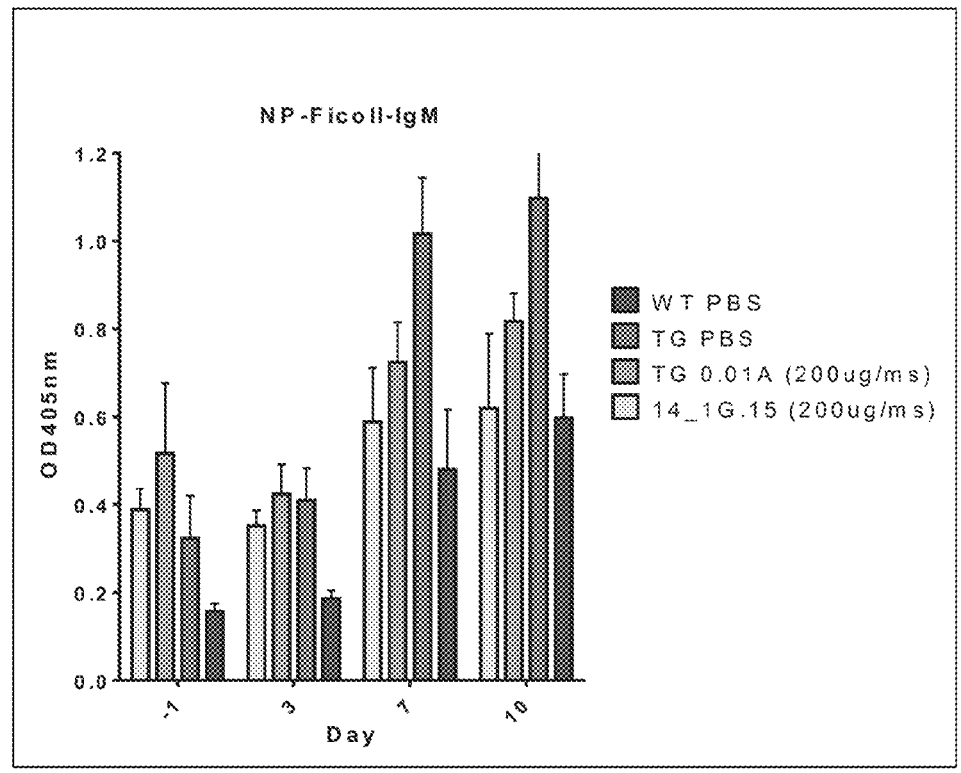

To demonstrate an in-vivo blocking effect of the APRIL analogue antibodies on APRIL function, we examined the ability of the antibodies to block the NP-Ficoll induced humoral response in mice. The mice used were 8-10 week old APRIL transgenic (TG) mice and wildtype (WT) littermates, both on a C57BL/6 background. The APRIL transgenic mice express human APRIL under the Lck-distal promoter, which directs transgene expression to mature thymocytes and peripheral T lymphocytes (Stein et al., 2002, J Clin Invest 109, 1587-98). The mice were bred in the animal facility of the Academic Medical Center and the experiment was approved by the institutional ethical committee. The mice were divided into several groups and treated as follows: WT mice were treated with PBS (200 µl) and 3 groups of APRIL transgenic mice were treated with the following molecules: hAPRIL.01A or 14_1 G.15 (200 µg/mouse on day −1 and day 3 in 200 µl PBS) or PBS. On day 0, mice were immunized with NP-Ficoll (day 0; 100 µl i.p. with 250 µg of the immunogen). Blood was collected via tail vein at day −1, 3, 7, 10. Anti-(4-hydroxy-nitrophenacetyl) (NP)-specific antibodies (IgM, IgG and IgAa/2) were assayed by ELISA using diluted sera as previously described (Hardenberg et al., Immunol Cell Biol, 86(6):530-4, (2008); Guadagnoli et al., 2011, Blood 117(25):6856-65). Briefly 96-well ELISA plates (Greiner) were coated with NP-BSA at 5 µg/ml (Biosearch Technologies) in sodium carbonate buffer (pH 9.6) overnight at 4° C. The wells were blocked with 1% BSA for 1 hr at 37° C. and incubated with diluted sera for 2 hrs at room temperature. HRP-conjugated isotype specific antibodies (Goat anti-mouse IgG, IgA and IgM—from Southern Biotech) were used as revealing antibodies. All dilutions were made in PBS/BSA 1%/Tween 20 0.05%. As apparent from FIG. 1, both hAPRIL.01A and 14_1 G.15 inhibited the T-cell independent B-cell responses in vivo. hAPRIL.01A inhibited this response less efficacious then 14_1 G.15. PBS and mouse IgG1 as an isotype-matched control, did not affect the IgA, IgM and IgG anti-NP response.

The invention claimed is:

1. A humanized antibody comprising a heavy chain variable region/light chain variable region pair selected from the group consisting of VH11/VL15, VH12/VL15, VH13/VL15, VH14/VL15, VH14_1/VL15, VH14_1C/VL15, VH14_1D/VL15, VH14_1E/VL15, and VH14_1G/VL15, wherein the antibody binds to human "A proliferation-inducing ligand" ("APRIL") protein.

2. A composition comprising an antibody of claim 1 and a pharmaceutically acceptable carrier or diluent.

3. A humanized antibody comprising a heavy chain variable region/light chain variable region pair, comprising:
  heavy chain complementary determining regions consisting of SEQ ID NO: 5, SEQ ID NO: 6, and SEQ ID NO: 7;
  light chain complementary determining regions consisting of SEQ ID NO: 8, SEQ ID NO: 9, and SEQ ID NO: 10; and
  framework regions having at least 90% sequence similarity to the framework regions of a heavy chain variable region/light chain variable region pair selected from the group consisting of VH11/VL15, VH12/VL15, VH13/VL15, VH14/VL15, VH14_1/VL15, VH14_1C/VL15, VH14_1D/VL15, VH14_1E/VL15, and VH14_1G/VL15 wherein the antibody binds to human "A proliferation-inducing ligand" ("APRIL") protein.

4. An antibody according to claim 3, wherein at least 90% sequence similarity is at least 90% sequence identity.

5. An antibody according to claim 3, wherein at least 90% sequence similarity is at least 95% sequence similarity.

6. An antibody according to claim 5, wherein at least 95% sequence similarity is at least 95% sequence identity.

7. An antibody according to claim 3, wherein the amino acid at position 72 of the heavy chain variable region is S.

8. An antibody according to claim 3, wherein the amino acid at position 67 of the heavy chain variable region is K and the amino acid at position 68 of the heavy chain variable region is A.

9. An antibody according to claim 4, wherein the amino acid at position 72 of the heavy chain variable region is S.

10. An antibody according to claim 4, wherein the amino acid at position 67 of the heavy chain variable region is K and the amino acid at position 68 of the heavy chain variable region is A.

11. An antibody according to claim 5, wherein the amino acid at position 72 of the heavy chain variable region is S.

12. An antibody according to claim 5, wherein the amino acid at position 67 of the heavy chain variable region is K and the amino acid at position 68 of the heavy chain variable region is A.

13. An antibody according to claim 6, wherein the amino acid at position 72 of the heavy chain variable region is S.

14. An antibody according to claim 6, wherein the amino acid at position 67 of the heavy chain variable region is K and the amino acid at position 68 of the heavy chain variable region is A.

15. A composition comprising an antibody according to claim 3 and a pharmaceutically acceptable carrier or diluent.

16. A composition comprising an antibody according to claim 4 and a pharmaceutically acceptable carrier or diluent.

17. A composition comprising an antibody according to claim 5 and a pharmaceutically acceptable carrier or diluent.

18. A composition comprising an antibody according to claim 6 and a pharmaceutically acceptable carrier or diluent.

19. A composition comprising an antibody according to claim 7 and a pharmaceutically acceptable carrier or diluent.

20. A composition comprising an antibody according to claim 8 and a pharmaceutically acceptable carrier or diluent.

21. A composition comprising an antibody according to claim 9 and a pharmaceutically acceptable carrier or diluent.

22. A composition comprising an antibody according to claim 10 and a pharmaceutically acceptable carrier or diluent.

23. A composition comprising an antibody according to claim 11 and a pharmaceutically acceptable carrier or diluent.

24. A composition comprising an antibody according to claim 12 and a pharmaceutically acceptable carrier or diluent.

25. A composition comprising an antibody according to claim 13 and a pharmaceutically acceptable carrier or diluent.

26. A composition comprising an antibody according to claim 14 and a pharmaceutically acceptable carrier or diluent.

* * * * *

SEQUENCE LISTING

<160> NUMBER OF SEQ ID NOS: 60

<210> SEQ ID NO 1
<211> LENGTH: 363
<212> TYPE: DNA
<213> ORGANISM: Mus musculus
<220> FEATURE:
<221> NAME/KEY: source
<222> LOCATION: 1..363
<223> OTHER INFORMATION: /mol_type="unassigned DNA"
      /organism="Mus musculus"

<400> SEQUENCE: 1

```
gaggtccagt tgcagcagtc tggacctgag ctggtaaagc ctggggcttc agtgaagatg      60
tcctgcaagg cttctggata cacattcact agctatgtga tgcactgggt gaagcagaag     120
cctgggcagg gccttgagtg gattggatat attaatcctt ataatgatgc tcctaaatac     180
aatgagaagt tcaaaggcaa ggccacagtg acttcagaca gtcctccgg cacagcctac     240 atggagctca gcagcctgac ctctgaggac tctgcggtct attactgtgc aaggggcttg     300
ggttacgccc tttactatgc tatggactac tggggtcaag gaacctcagt caccgtctcc     360
tca                                                                    363
```

<210> SEQ ID NO 2
<211> LENGTH: 321
<212> TYPE: DNA
<213> ORGANISM: Mus musculus
<220> FEATURE:

```
<221> NAME/KEY: source
<222> LOCATION: 1..321
<223> OTHER INFORMATION: /mol_type="unassigned DNA"
      /organism="Mus musculus"

<400> SEQUENCE: 2
```

| | | | | | |
|---|---|---|---|---|---|
| gacattgtga | tgacccagtc | tcaaaaattc | aagtccacat | cagtaggaga | cagggtcagc | 60 |
| gtcacctgca | aggccagtca | gaatgtgggt | aataatgtag | cctggtatca | acagaaagca | 120 |
| gggcaatctc | ctaaagcact | gattcctcg | gcatccaacc | gtgacagtgg | agtccctgat | 180 |
| cgcttcacag | gcagtggatc | tgggacagat | ttcactctca | ccatcagcaa | tgtgcagtct | 240 |
| gaagacttgg | cagactattt | ctgtcagcaa | tataacatct | atccattcac | gttcggctcg | 300 |
| gggacaaagt | tggaaataaa | a | | | | 321 |

```
<210> SEQ ID NO 3
<211> LENGTH: 121
<212> TYPE: PRT
<213> ORGANISM: Mus musculus

<400> SEQUENCE: 3
```

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Ala Pro Lys Tyr Asn Glu Lys Phe
    50                  55                  60

Lys Gly Lys Ala Thr Val Thr Ser Asp Lys Ser Ser Gly Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Ser Val Thr Val Ser Ser
        115                 120

```
<210> SEQ ID NO 4
<211> LENGTH: 107
<212> TYPE: PRT
<213> ORGANISM: Mus musculus

<400> SEQUENCE: 4
```

Asp Ile Val Met Thr Gln Ser Gln Lys Phe Lys Ser Thr Ser Val Gly
1               5                   10                  15

Asp Arg Val Ser Val Thr Cys Lys Ala Ser Gln Asn Val Gly Asn Asn
            20                  25                  30

Val Ala Trp Tyr Gln Gln Lys Ala Gly Gln Ser Pro Lys Ala Leu Ile
        35                  40                  45

Ser Ser Ala Ser Asn Arg Asp Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ile Tyr Pro Phe
                85                  90                  95

Thr Phe Gly Ser Gly Thr Lys Leu Glu Ile Lys
            100                 105

<210> SEQ ID NO 5
<211> LENGTH: 8
<212> TYPE: PRT
<213> ORGANISM: Mus musculus

<400> SEQUENCE: 5

Gly Tyr Thr Phe Thr Ser Tyr Val
1               5

<210> SEQ ID NO 6
<211> LENGTH: 16
<212> TYPE: PRT
<213> ORGANISM: Mus musculus

<400> SEQUENCE: 6

Tyr Ile Asn Pro Tyr Asn Asp Ala Pro Lys Tyr Asn Glu Lys Phe Lys
1               5                   10                  15

<210> SEQ ID NO 7
<211> LENGTH: 12
<212> TYPE: PRT
<213> ORGANISM: Mus musculus

<400> SEQUENCE: 7

Gly Leu Gly Tyr Ala Leu Tyr Tyr Ala Met Asp Tyr
1               5                   10

<210> SEQ ID NO 8
<211> LENGTH: 11
<212> TYPE: PRT
<213> ORGANISM: Mus musculus

<400> SEQUENCE: 8

Lys Ala Ser Gln Asn Val Gly Asn Asn Val Ala
1               5                   10

<210> SEQ ID NO 9
<211> LENGTH: 7
<212> TYPE: PRT
<213> ORGANISM: Mus musculus

<400> SEQUENCE: 9

Ser Ala Ser Asn Arg Asp Ser
1               5

<210> SEQ ID NO 10
<211> LENGTH: 10
<212> TYPE: PRT
<213> ORGANISM: Mus musculus

<400> SEQUENCE: 10

Gln Gln Tyr Asn Ile Tyr Pro Phe Thr Phe
1               5                   10

<210> SEQ ID NO 11
<211> LENGTH: 363
<212> TYPE: DNA
<213> ORGANISM: Artificial Sequence
<220> FEATURE:
<221> NAME/KEY: source
<222> LOCATION: 1..363
<223> OTHER INFORMATION: /mol_type="unassigned DNA"
      /note="Engineered immunoglobulin VH sequence"
      /organism="Artificial Sequence"

<400> SEQUENCE: 11

| | | |
|---|---|---|
| caggtccagc ttgtgcagtc tggggctgag gtgaagaagc ctggggcctc agtgaaggtt | 60 |
| tcctgcaagg cttctggata cacattcact agctatgtga tgcattgggt gcgccaggcc | 120 |
| cccggacaaa ggcttgagtg gatgggatat attaatcctt ataatgatgc tcctaaatac | 180 |
| aatgagaagt tcaaaggcag agtcaccatt accagggaca catccgcgag cacagcctac | 240 |
| atggagctga gcagcctgag atctgaagac acggctgtgt attactgtgc gagaggcttg | 300 |
| ggttacgccc tttactatgc tatggactac tggggccaag gaccacggt caccgtctcc | 360 |
| tca | 363 |

<210> SEQ ID NO 12
<211> LENGTH: 121
<212> TYPE: PRT
<213> ORGANISM: Artificial Sequence
<220> FEATURE:
<223> OTHER INFORMATION: Engineered immunoglobulin VH sequence

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Met
            35                  40                  45

Gly Tyr Ile Asn Pro Tyr Asn Asp Ala Pro Lys Tyr Asn Glu Lys Phe
        50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Thr Val Thr Val Ser Ser
        115                 120

<210> SEQ ID NO 13
<211> LENGTH: 363
<212> TYPE: DNA
<213> ORGANISM: Artificial Sequence
<220> FEATURE:
<221> NAME/KEY: source
<222> LOCATION: 1..363
<223> OTHER INFORMATION: /mol_type="unassigned DNA"
      /note="Engineered immunoglobulin VH sequence"
      /organism="Artificial Sequence"

<400> SEQUENCE: 13

| | | |
|---|---|---|
| caggtccagc ttgtgcagtc tggggctgag gtgaagaagc ctggggcctc agtgaaggtc | 60 |
| tcctgcaagg cttctggata cacattcact agctatgtga tgcactgggt gcgacaggcc | 120 |
| cctggacaag ggcttgagtg gatgggatat attaatcctt ataatgatgc tcctaaatac | 180 |
| aatgagaagt tcaaaggcag ggtcaccatg accagggaca cgtccatcag cacagcctac | 240 |
| atggagctga gcaggctgag atctgacgac acggccgtgt attactgtgc gagaggcttg | 300 |
| ggttacgccc tttactatgc tatggactac tggggccaag gaccacggt caccgtctcg | 360 |
| agc | 363 |

```
<210> SEQ ID NO 14
<211> LENGTH: 121
<212> TYPE: PRT
<213> ORGANISM: Artificial Sequence
<220> FEATURE:
<223> OTHER INFORMATION: Engineered immunoglobulin VH sequence

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Ala Pro Lys Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Thr Val Thr Val Ser Ser
        115                 120

<210> SEQ ID NO 15
<211> LENGTH: 363
<212> TYPE: DNA
<213> ORGANISM: Artificial Sequence
<220> FEATURE:
<221> NAME/KEY: source
<222> LOCATION: 1..363
<223> OTHER INFORMATION: /mol_type="unassigned DNA"
      /note="Engineered immunoglobulin VH sequence"
      /organism="Artificial Sequence"

<400> SEQUENCE: 15
caggtccagc ttgtgcagtc tggggctgag gtgaagaagc ctggggcctc agtgaaggtt     60
tcctgcaagg catctggata cacattcact agctatgtga tgcactgggt gcgacaggcc    120
cctggacaag gcttgagtg gatgggatat attaatcctt ataatgatgc tcctaaatac    180
aatgagaagt tcaaaggcag agtcaccatg accaggaca cgtccacgag cacagtctac    240
atggagctga gcagcctgag atctgaggac acggccgtgt attactgtgc gagaggcttg    300
ggttacgccc tttactatgc tatggactac tggggccaag gacaatggt caccgtctcg    360 agc                                                                  363

<210> SEQ ID NO 16
<211> LENGTH: 121
<212> TYPE: PRT
<213> ORGANISM: Artificial Sequence
<220> FEATURE:
<223> OTHER INFORMATION: Engineered immunoglobulin VH sequence

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45
```

```
Gly Tyr Ile Asn Pro Tyr Asn Asp Ala Pro Lys Tyr Asn Glu Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Ala Leu Tyr Tyr Ala Met Asp Tyr Trp Gly
                100                 105                 110

Gln Gly Thr Met Val Thr Val Ser Ser
            115                 120

<210> SEQ ID NO 17
<211> LENGTH: 363
<212> TYPE: DNA
<213> ORGANISM: Artificial Sequence
<220> FEATURE:
<221> NAME/KEY: source
<222> LOCATION: 1..363
<223> OTHER INFORMATION: /mol_type="unassigned DNA"
      /note="Engineered immunoglobulin VH sequence"
      /organism="Artificial Sequence"

<400> SEQUENCE: 17
caggtccagc ttgtgcagtc tggggctgag gtgaagaagc ccggcgccag cgtgaaggtg    60
agctgcaagg ccagcggata cacattcact agctatgtga tgcactgggt gagacaggcc   120
cccggccagg gcctggagtg gatgggctat attaatcctt ataatgatgc tcctaaatac   180
aatgagaagt tcaaaggcag agtgaccatg accagagaca ccagcgccag caccgcctac   240
atggagctga gcagcctgag aagcgacgac accgccgtgt actactgcgc cagaggcttg   300
ggttacgccc tttactatgc tatggactac tggggccagg gcaccaccgt gaccgtgagc   360
agc                                                                 363

<210> SEQ ID NO 18
<211> LENGTH: 121
<212> TYPE: PRT
<213> ORGANISM: Artificial Sequence
<220> FEATURE:
<223> OTHER INFORMATION: Engineered immunoglobulin VH sequence

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Gly Leu Glu Trp Met
            35                  40                  45

Gly Tyr Ile Asn Pro Tyr Asn Asp Ala Pro Lys Tyr Asn Glu Lys Phe
        50                  55                  60

Lys Gly Arg Val Thr Met Thr Arg Asp Thr Ser Ala Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Leu Gly Tyr Ala Leu Tyr Tyr Ala Met Asp Tyr Trp Gly
                100                 105                 110

Gln Gly Thr Thr Val Thr Val Ser Ser
            115                 120
```

```
<210> SEQ ID NO 19
<211> LENGTH: 321
<212> TYPE: DNA
<213> ORGANISM: Artificial Sequence
<220> FEATURE:
<221> NAME/KEY: source
<222> LOCATION: 1..321
<223> OTHER INFORMATION: /mol_type="unassigned DNA"
      /note="Engineered immunoglobulin VL sequence"
      /organism="Artificial Sequence"

<400> SEQUENCE: 19
gacattgtga tgacccagtc tcaaaaattc atgtccacat ccgtaggaga cagggtcagc    60
atcacctgca aggccagtca gaatgtgggt aataatgtag cctggtatca acagaaacca   120
ggacaatctc ctaaattgct gatttactcg gcatccaacc gtgacagtgg agtccctgat   180
cgcttctcag gcagtgggtc tgggacagat ttcactctca ccatcagcaa tatgcagtct   240
gaagacctgg cagattattt ctgccagcaa tataacatct atccattcac gttcggaggg   300
gggaccaagc tggaaatcaa a                                             321

<210> SEQ ID NO 20
<211> LENGTH: 107
<212> TYPE: PRT
<213> ORGANISM: Artificial Sequence
<220> FEATURE:
<223> OTHER INFORMATION: Engineered immunoglobulin VL sequence

<400> SEQUENCE: 20

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Asn Asn
            20                  25                  30

Val Ala Trp Tyr Gln Gln Lys Pro Gly Gln Ser Pro Lys Leu Leu Ile
        35                  40                  45

Tyr Ser Ala Ser Asn Arg Asp Ser Gly Val Pro Asp Arg Phe Ser Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asn Ile Tyr Pro Phe
                85                  90                  95

Thr Phe Gly Gly Gly Thr Lys Leu Glu Ile Lys
            100                 105

<210> SEQ ID NO 21
<211> LENGTH: 321
<212> TYPE: DNA
<213> ORGANISM: Artificial Sequence
<220> FEATURE:
<221> NAME/KEY: source
<222> LOCATION: 1..321
<223> OTHER INFORMATION: /mol_type="unassigned DNA"
      /note="Engineered immunoglobulin VL sequence"
      /organism="Artificial Sequence"

<400> SEQUENCE: 21
gacattgtga tgacccagtc tcaaaaattc atgcccacat cagtaggaga cagggtcagc    60
gtcacctgca aggccagtca gaatgtgggt aataatgtag cctggtatca acagaaacca   120
gggcaatctc ctaaagcact gatttactcg gcatccaacc gtgacagtgg agtccctgat   180
cgcttcacag gcagtggatc tgggacagat ttcactctca ccatcaccaa tgtgcagtct   240
gaagacttgg cagagtattt ctgtcagcaa tataacatct atccattcac gttcggtgct   300
```
gggaccaagc tggagctgaa a                                                       321

<210> SEQ ID NO 22
<211> LENGTH: 107
<212> TYPE: PRT
<213> ORGANISM: Artificial Sequence
<220> FEATURE:
<223> OTHER INFORMATION: Engineered immunoglobulin VL sequence

<400> SEQUENCE: 22

Asp Ile Val Met Thr Gln Ser Gln Lys Phe Met Pro Thr Ser Val Gly
1               5                   10                  15

Asp Arg Val Ser Val Thr Cys Lys Ala Ser Gln Asn Val Gly Asn Asn
            20                  25                  30

Val Ala Trp Tyr Gln Gln Lys Pro Gly Gln Ser Pro Lys Ala Leu Ile
        35                  40                  45

Tyr Ser Ala Ser Asn Arg Asp Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asn Ile Tyr Pro Phe
                85                  90                  95

Thr Phe Gly Ala Gly Thr Lys Leu Glu Leu Lys
            100                 105

<210> SEQ ID NO 23
<211> LENGTH: 321
<212> TYPE: DNA
<213> ORGANISM: Artificial Sequence
<220> FEATURE:
<221> NAME/KEY: source
<222> LOCATION: 1..321
<223> OTHER INFORMATION: /mol_type="unassigned DNA"
      /note="Engineered immunoglobulin VL sequence"
      /organism="Artificial Sequence"

<400> SEQUENCE: 23
gaaattgtgt tgacgcagtc tccttccacc cagtctgcat ctgtaggaga cagagtcacc    60
atcacttgca aggccagtca gaatgtgggt aataatgtag cctggtatca gcagaaacca   120
gggaaagccc ctaaactcct aatctattcg catccaacc gtgacagtgg ggtcccatca    180
aggttcagcg gcagtggatc tgggacagag ttcactctca ccatcagcag cctgcagcct   240
gatgattttg caacttatta ctgccagcaa tataacatct atccattcac gtttggccag   300
gggaccaagc tggagatcaa a                                             321

<210> SEQ ID NO 24
<211> LENGTH: 107
<212> TYPE: PRT
<213> ORGANISM: Artificial Sequence
<220> FEATURE:
<223> OTHER INFORMATION: Engineered immunoglobulin VL sequence

<400> SEQUENCE: 24

Glu Ile Val Leu Thr Gln Ser Pro Ser Thr Gln Ser Ala Ser Val Gly
1               5                   10                  15

Asp Arg Val Thr Ile Thr Cys Lys Ala Ser Gln Asn Val Gly Asn Asn
            20                  25                  30

Val Ala Trp Tyr Gln Gln Lys Pro Gly Lys Ala Pro Lys Leu Leu Ile
        35                  40                  45

Tyr Ser Ala Ser Asn Arg Asp Ser Gly Val Pro Ser Arg Phe Ser Gly
            50                  55                  60

Ser Gly Ser Gly Thr Glu Phe Thr Leu Thr Ile Ser Ser Leu Gln Pro
 65                 70                  75                  80

Asp Asp Phe Ala Thr Tyr Tyr Cys Gln Gln Tyr Asn Ile Tyr Pro Phe
                85                  90                  95

Thr Phe Gly Gln Gly Thr Lys Leu Glu Ile Lys
            100                 105

<210> SEQ ID NO 25
<211> LENGTH: 321
<212> TYPE: DNA
<213> ORGANISM: Artificial Sequence
<220> FEATURE:
<221> NAME/KEY: source
<222> LOCATION: 1..321
<223> OTHER INFORMATION: /mol_type="unassigned DNA"
      /note="Engineered immunoglobulin VL sequence"
      /organism="Artificial Sequence"

<400> SEQUENCE: 25
gacatcgtga tgacccagtc tccttctacc ctgtctgcat ctgtgggaga cagagtcacc      60
atcacttgca aggccagtca gaatgtgggt aataatgtag cctggtatca gcagaaacca     120
gggaaagccc ctaagctcct gatctattcg catccaacc gtgacagtgg ggtcccatca      180
aggttcagcg gcagtggatc tgggacagag ttcactctca ccatcagcag cctgcagcct     240
gatgattttg caacttatta ctgccagcaa tataacatct atccattcac gtttggccag     300
gggaccaagc tggagatcaa a                                               321

<210> SEQ ID NO 26
<211> LENGTH: 107
<212> TYPE: PRT
<213> ORGANISM: Artificial Sequence
<220> FEATURE:
<223> OTHER INFORMATION: Engineered immunoglobulin VL sequence

<400> SEQUENCE: 26

Asp Ile Val Met Thr Gln Ser Pro Ser Thr Leu Ser Ala Ser Val Gly
  1               5                  10                  15

Asp Arg Val Thr Ile Thr Cys Lys Ala Ser Gln Asn Val Gly Asn Asn
                20                  25                  30

Val Ala Trp Tyr Gln Gln Lys Pro Gly Lys Ala Pro Lys Leu Leu Ile
            35                  40                  45

Tyr Ser Ala Ser Asn Arg Asp Ser Gly Val Pro Ser Arg Phe Ser Gly
            50                  55                  60

Ser Gly Ser Gly Thr Glu Phe Thr Leu Thr Ile Ser Ser Leu Gln Pro
 65                 70                  75                  80

Asp Asp Phe Ala Thr Tyr Tyr Cys Gln Gln Tyr Asn Ile Tyr Pro Phe
                85                  90                  95

Thr Phe Gly Gln Gly Thr Lys Leu Glu Ile Lys
            100                 105

<210> SEQ ID NO 27
<211> LENGTH: 321
<212> TYPE: DNA
<213> ORGANISM: Artificial Sequence
<220> FEATURE:
<221> NAME/KEY: source
<222> LOCATION: 1..321
<223> OTHER INFORMATION: /mol_type="unassigned DNA"
      /note="Engineered immunoglobulin VL sequence"

/organism="Artificial Sequence"

<400> SEQUENCE: 27

```
gatatcctga tgacccagtc tcaaaaaatc atgcccacat cagtgggaga cagggtcagc    60
gtcacctgca aggccagtca gaatgtgggt aataatgtag cctggtatca acagaaacca   120
ggacagtctc ctaaagcact gatttactcg gcatccaacc gtgacagtgg agtccctgat   180
cgcttcacag gcagtggatc tgggacagat tcactctca ccatcaccaa tgtgcagtct   240
gaggacttgg cagagtattt ctgtcagcaa tataacatct atccattcac gttcggtgct   300
gggaccaagc tggacctgaa a                                             321
```

<210> SEQ ID NO 28
<211> LENGTH: 107
<212> TYPE: PRT
<213> ORGANISM: Artificial Sequence
<220> FEATURE:
<223> OTHER INFORMATION: Engineered immunoglobulin VL sequence

<400> SEQUENCE: 28

```
Asp Ile Leu Met Thr Gln Ser Gln Lys Ile Met Pro Thr Ser Val Gly
1               5                   10                  15

Asp Arg Val Ser Val Thr Cys Lys Ala Ser Gln Asn Val Gly Asn Asn
            20                  25                  30

Val Ala Trp Tyr Gln Gln Lys Pro Gly Gln Ser Pro Lys Ala Leu Ile
        35                  40                  45

Tyr Ser Ala Ser Asn Arg Asp Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asn Ile Tyr Pro Phe
                85                  90                  95

Thr Phe Gly Ala Gly Thr Lys Leu Asp Leu Lys
            100                 105
```

<210> SEQ ID NO 29
<211> LENGTH: 321
<212> TYPE: DNA
<213> ORGANISM: Artificial Sequence
<220> FEATURE:
<221> NAME/KEY: source
<222> LOCATION: 1..321
<223> OTHER INFORMATION: /mol_type="unassigned DNA"
      /note="Engineered immunoglobulin VL sequence"
      /organism="Artificial Sequence"

<400> SEQUENCE: 29

```
gacatcgtga tgacccagtc tccttccacc ctgtctgcat ctgtaggaga cagagtcacc    60
atcacttgca aggccagtca gaatgtgggt aataatgtag cctggtatca gcagaaacca   120
gggaaagccc ctaagctcct gatctcttcg gcatccaacc gtgacagtgg ggtcccatca   180
aggttcagcg gcagtggatc tgggacagag ttcactctca ccatcagcag cctgcagcct   240
gatgattttg caacttattt ctgccagcaa tataacatct atccattcac gtttggccag   300
gggaccaagc tggagatcaa a                                             321
```

<210> SEQ ID NO 30
<211> LENGTH: 107
<212> TYPE: PRT
<213> ORGANISM: Artificial Sequence
<220> FEATURE:

<223> OTHER INFORMATION: Engineered immunoglobulin VL sequence

<400> SEQUENCE: 30

Asp Ile Val Met Thr Gln Ser Pro Ser Thr Leu Ser Ala Ser Val Gly
1               5                   10                  15

Asp Arg Val Thr Ile Thr Cys Lys Ala Ser Gln Asn Val Gly Asn Asn
            20                  25                  30

Val Ala Trp Tyr Gln Gln Lys Pro Gly Lys Ala Pro Lys Leu Leu Ile
        35                  40                  45

Ser Ser Ala Ser Asn Arg Asp Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Asn Ile Tyr Pro Phe
                85                  90                  95

Thr Phe Gly Gln Gly Thr Lys Leu Glu Ile Lys
            100                 105

<210> SEQ ID NO 31
<211> LENGTH: 363
<212> TYPE: DNA
<213> ORGANISM: Artificial Sequence
<220> FEATURE:
<221> NAME/KEY: source
<222> LOCATION: 1..363
<223> OTHER INFORMATION: /mol_type="unassigned DNA"
      /note="Engineered immunoglobulin VH sequence"
      /organism="Artificial Sequence"

<400> SEQUENCE: 31
caggtccagc ttgtgcagtc tggggctgag gtgaagaagc ccggcgccag cgtgaaggtg     60
agctgcaagg ccagcggata cacattcact agctatgtga tgcactgggt gagacaggcc    120
cccggccagg gcctggagtg gatgggctat attaatcctt ataatgatgc tcctaaatac    180
aatgagaagt tcaaaggcag agtgaccatg accagtgaca ccagcgccag caccgcctac    240
atggagctga gcagcctgag aagcgacgac accgccgtgt actactgcgc cagaggcttg    300
ggttacgccc tttactatgc tatggactac tggggccagg gcaccaccgt gaccgtgagc    360
agc                                                                  363

<210> SEQ ID NO 32
<211> LENGTH: 121
<212> TYPE: PRT
<213> ORGANISM: Artificial Sequence
<220> FEATURE:
<223> OTHER INFORMATION: Engineered immunoglobulin VH sequence

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Ala Pro Lys Tyr Asn Glu Lys Phe
    50                  55                  60

Lys Gly Arg Val Thr Met Thr Ser Asp Thr Ser Ala Ser Thr Ala Tyr
65                  70                  75                  80

Met Glu Leu Ser Ser Leu Arg Ser Asp Asp Thr Ala Val Tyr Tyr Cys

```
                        85                  90                  95
Ala Arg Gly Leu Gly Tyr Ala Leu Tyr Tyr Ala Met Asp Tyr Trp Gly
            100                 105                 110

Gln Gly Thr Thr Val Thr Val Ser Ser
        115                 120
```

<210> SEQ ID NO 33
<211> LENGTH: 363
<212> TYPE: DNA
<213> ORGANISM: Artificial Sequence
<220> FEATURE:
<221> NAME/KEY: source
<222> LOCATION: 1..363
<223> OTHER INFORMATION: /mol_type="unassigned DNA"
      /note="Engineered immunoglobulin VH sequence"
      /organism="Artificial Sequence"

<400> SEQUENCE: 33

```
caggtccagc ttgtgcagtc tggggctgag gtgaagaagc ccggcgccag cgtgaaggtg    60
agctgcaagg ccagcggata cacattcact agctatgtga tgcactgggt gagacaggcc   120
cccggccagg gcctggagtg gatgggctat attaatcctt ataatgatgc tcctaaatac   180
aatgagaagt tcaaaggcag agtgaccatc accagtgaca ccagcgccag caccgcctac   240
atggagctga gcagcctgag aagcgacgac accgccgtgt actactgcgc cagaggcttg   300
ggttacgccc tttactatgc tatggactac tggggccagg gcaccaccgt gaccgtgagc   360
agc                                                                363
```

<210> SEQ ID NO 34
<211> LENGTH: 121
<212> TYPE: PRT
<213> ORGANISM: Artificial Sequence
<220> FEATURE:
<223> OTHER INFORMATION: Engineered immunoglobulin VH sequence

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Ala Pro Lys Tyr Asn Glu Lys Phe
    50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Thr Val Thr Val Ser Ser
        115                 120
```

<210> SEQ ID NO 35
<211> LENGTH: 363
<212> TYPE: DNA
<213> ORGANISM: Artificial Sequence
<220> FEATURE:
<221> NAME/KEY: source
<222> LOCATION: 1..363
<223> OTHER INFORMATION: /mol_type="unassigned DNA"

/note="Engineered immunoglobulin VH sequence"
/organism="Artificial Sequence"

<400> SEQUENCE: 35

```
caggtccagc ttgtgcagtc tggggctgag gtgaagaagc ccggcgccag cgtgaaggtg        60
agctgcaagg ccagcggata cacattcact agctatgtga tgcactgggt gagacaggcc       120
cccggccagg gcctggagtg gatgggctat attaatcctt ataatgatgc tcctaaatac       180
aatgagaagt tcaaaggcag agtgaccatg accagtgaca gagcgccag caccgcctac        240
atggagctga gcagcctgag aagcgacgac accgccgtgt actactgcgc cagaggcttg       300
ggttacgccc tttactatgc tatggactac tggggccagg gcaccaccgt gaccgtgagc       360
agc                                                                     363
```

<210> SEQ ID NO 36
<211> LENGTH: 121
<212> TYPE: PRT
<213> ORGANISM: Artificial Sequence
<220> FEATURE:
<223> OTHER INFORMATION: Engineered immunoglobulin VH sequence

<400> SEQUENCE: 36

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Val Met His Trp Val Arg Gln Ala Pro Gly Gln Gly Leu Glu Trp Met
        35                  40                  45
Gly Tyr Ile Asn Pro Tyr Asn Asp Ala Pro Lys Tyr Asn Glu Lys Phe
    50                  55                  60
Lys Gly Arg Val Thr Met Thr Ser Asp Lys Ser Ala Ser Thr Ala Tyr
65                  70                  75                  80
Met Glu Leu Ser Ser Leu Arg Ser Asp Asp Thr Ala Val Tyr Tyr Cys
                85                  90                  95
Ala Arg Gly Leu Gly Tyr Ala Leu Tyr Tyr Ala Met Asp Tyr Trp Gly
            100                 105                 110
Gln Gly Thr Thr Val Thr Val Ser Ser
        115                 120
```

<210> SEQ ID NO 37
<211> LENGTH: 363
<212> TYPE: DNA
<213> ORGANISM: Artificial Sequence
<220> FEATURE:
<221> NAME/KEY: source
<222> LOCATION: 1..363
<223> OTHER INFORMATION: /mol_type="unassigned DNA"
       /note="Engineered immunoglobulin VH sequence"
       /organism="Artificial Sequence"

<400> SEQUENCE: 37

```
gaggtccagc ttgtgcagtc tggggctgag gtgaagaagc ccggcgccag cgtgaaggtg        60
agctgcaagg ccagcggata cacattcact agctatgtga tgcactgggt gagacaggcc       120
cccggccagg gcctggagtg gatgggctat attaatcctt ataatgatgc tcctaaatac       180
aatgagaagt tcaaaggcag agtgaccatg accagtgaca ccagcgccag caccgcctac       240
atggagctga gcagcctgag aagcgacgac accgccgtgt actactgcgc cagaggcttg       300
ggttacgccc tttactatgc tatggactac tggggccagg gcaccaccgt gaccgtgagc       360
``` agc                                                              363

<210> SEQ ID NO 38
<211> LENGTH: 121
<212> TYPE: PRT
<213> ORGANISM: Artificial Sequence
<220> FEATURE:
<223> OTHER INFORMATION: Engineered immunoglobulin VH sequence

<400> SEQUENCE: 38

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Ala Pro Lys Tyr Asn Glu Lys Phe
    50                  55                  60

Lys Gly Arg Val Thr Met Thr Ser Asp Thr Ser Ala Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Thr Val Thr Val Ser Ser
        115                 120

<210> SEQ ID NO 39
<211> LENGTH: 363
<212> TYPE: DNA
<213> ORGANISM: Artificial Sequence
<220> FEATURE:
<221> NAME/KEY: source
<222> LOCATION: 1..363
<223> OTHER INFORMATION: /mol_type="unassigned DNA"
      /note="Engineered immunoglobulin VH sequence"
      /organism="Artificial Sequence"

<400> SEQUENCE: 39
caggtccagc ttgtgcagtc tggggctgag gtgaagaagc ccggcgccag cgtgaaggtg      60
agctgcaagg ccagcggata cacattcact agctatgtga tgcactgggt gagacaggcc     120
cccggccagg gcctggagtg gatgggctat attaatcctt ataatgatgc tcctaaatac     180
aatgagaagt tcaaaggcaa agcgaccatg accagtgaca ccagcgccag caccgcctac     240
atggagctga gcagcctgag aagcgacgac accgccgtgt actactgcgc cagaggcttg     300
ggttacgccc tttactatgc tatggactac tggggccagg gcaccaccgt gaccgtgagc     360
agc                                                              363

<210> SEQ ID NO 40
<211> LENGTH: 121
<212> TYPE: PRT
<213> ORGANISM: Artificial Sequence
<220> FEATURE:
<223> OTHER INFORMATION: Engineered immunoglobulin VH sequence

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
          35                  40                  45

Gly Tyr Ile Asn Pro Tyr Asn Asp Ala Pro Lys Tyr Asn Glu Lys Phe
        50                  55                  60

Lys Gly Lys Ala Thr Met Thr Ser Asp Thr Ser Ala Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Thr Val Thr Val Ser Ser
            115                 120

<210> SEQ ID NO 41
<211> LENGTH: 1344
<212> TYPE: DNA
<213> ORGANISM: Artificial Sequence
<220> FEATURE:
<221> NAME/KEY: source
<222> LOCATION: 1..1344
<223> OTHER INFORMATION: /mol_type="unassigned DNA"
      /note="Engineered immunoglobulin heavy chain sequence"
      /organism="Artificial Sequence"

<400> SEQUENCE: 41
caggtccagc ttgtgcagtc tgggcctgag gtgaagaagc ctggggcctc agtgaaggtt      60
tcctgcaagg cttctggata cacattcact agctatgtga tgcattgggt gcgccaggcc     120
cccggacaaa ggcttgagtg gatgggatat attaatcctt ataatgatgc tcctaaatac     180
aatgagaagt tcaaaggcag agtcaccatt accagggaca catccgcgag cacagcctac     240
atggagctga gcagcctgag atctgaagac acggctgtgt attactgtgc gagaggcttg     300
ggttacgccc tttactatgc tatggactac tggggccaag gaccacggt caccgtctcc      360 tcagcatcca ccaagggccc atccgtcttc cccctggcgc cctgctccag gagcacctcc     420
gagagcacag ccgccctggg ctgcctggtc aaggactact ccccgaacc ggtgacggtg      480 tcgtggaact caggcgccct gaccagcggc gtgcacacct tcccggctgt cctacagtcc     540
tcaggactct actccctcag cagcgtggtg accgtgccct ccagcagctt gggcacgaag     600
acctacacct gcaacgtaga tcacaagccc agcaacacca aggtggacaa gagagttgag     660
tccaaatatg gtccccatg cccaccatgc ccagcacctg agttcctggg gggaccatca     720
gtcttcctgt tccccccaaa acccaaggac actctcatga tctcccggac ccctgaggtc     780
acgtgcgtgg tggtggacgt gagccaggaa gaccccgagg tccagttcaa ctggtacgtg     840
gatggcgtgg aggtgcataa tgccaagaca aagccgcggg aggagcagtt caacagcacg     900
taccgtgtgg tcagcgtcct caccgtcctg caccaggact ggctgaacgg caaggagtac     960
aagtgcaagg tctccaacaa aggcctcccg tcctccatcg agaaaccat ctccaaagcc     1020 aaagggcagc ccgagagcc acaggtgtac accctgcccc catcccagga ggagatgacc     1080
aagaaccagg tcagcctgac ctgcctggtc aaaggcttct accccagcga catcgccgtg     1140
gagtgggaga gcaatgggca gccggagaac aactacaaga ccacgcctcc cgtgctggac     1200
tccgacggct ccttcttcct ctacagcagg ctaaccgtgg acaagagcag gtggcaggag     1260
gggaatgtct tctcatgctc cgtgatgcat gaggctctgc acaaccacta cacacagaag     1320
agcctctccc tgtctctggg taaa                                           1344

```
<210> SEQ ID NO 42
<211> LENGTH: 448
<212> TYPE: PRT
<213> ORGANISM: Artificial Sequence
<220> FEATURE:
<223> OTHER INFORMATION: Engineered immunoglobulin heavy chain sequence

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Ala Pro Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365
```

| | | | | | | | | | | | |
|---|---|---|---|---|---|---|---|---|---|---|---|
|Leu|Val|Lys|Gly|Phe|Tyr|Pro|Ser|Asp|Ile|Ala|Val Glu Trp Glu Ser|
| |370| | | |375| | | |380| | |

| | | | | | | | | | | | |
|---|---|---|---|---|---|---|---|---|---|---|---|
|Asn|Gly|Gln|Pro|Glu|Asn|Asn|Tyr|Lys|Thr|Thr|Pro Pro Val Leu Asp|
|385| | | |390| | | |395| | |400|

| | | | | | | | | | | | |
|---|---|---|---|---|---|---|---|---|---|---|---|
|Ser|Asp|Gly|Ser|Phe|Phe|Leu|Tyr|Ser|Arg|Leu|Thr Val Asp Lys Ser|
| | | | |405| | | |410| | |415|

| | | | | | | | | | | | |
|---|---|---|---|---|---|---|---|---|---|---|---|
|Arg|Trp|Gln|Glu|Gly|Asn|Val|Phe|Ser|Cys|Ser|Val Met His Glu Ala|
| | | |420| | | |425| | | |430|

| | | | | | | | | | | |
|---|---|---|---|---|---|---|---|---|---|---|
|Leu|His|Asn|His|Tyr|Thr|Gln|Lys|Ser|Leu|Ser Leu Ser Leu Gly Lys|
| | |435| | | |440| | | |445|

<210> SEQ ID NO 43
<211> LENGTH: 1344
<212> TYPE: DNA
<213> ORGANISM: Artificial Sequence
<220> FEATURE:
<221> NAME/KEY: source
<222> LOCATION: 1..1344
<223> OTHER INFORMATION: /mol_type="unassigned DNA"
   /note="Engineered immunoglobulin heavy chain sequence"
   /organism="Artificial Sequence"

<400> SEQUENCE: 43

| | |
|---|---|
|caggtccagc ttgtgcagtc tggggctgag gtgaagaagc ctggggcctc agtgaaggtc|60|
|tcctgcaagg cttctggata cacattcact agctatgtga tgcactgggt gcgacaggcc|120|
|cctggacaag ggcttgagtg gatgggatat attaatcctt ataatgatgc tcctaaatac|180|
|aatgagaagt tcaaaggcag ggtcaccatg accagggaca cgtccatcag cacagcctac|240|
|atggagctga gcaggctgag atctgacgac acggccgtgt attactgtgc gagaggcttg|300|
|ggttacgccc tttactatgc tatggactac tggggccaag gaccacggt caccgtctcg|360|
|agcgcatcca ccaagggccc atccgtcttc cccctggcgc cctgctccag gagcacctcc|420|
|gagagcacag ccgccctggg ctgcctggtc aaggactact ccccgaacc ggtgacggtg|480|
|tcgtggaact caggcgccct gaccagcggc gtgcacacct tcccggctgt cctacagtcc|540|
|tcaggactct actccctcag cagcgtggtg accgtgccct ccagcagctt gggcacgaag|600|
|acctacacct gcaacgtaga tcacaagccc agcaacacca aggtggacaa gagagttgag|660|
|tccaaatatg gtcccccatg cccaccatgc ccagcacctg agttcctggg gggaccatca|720|
|gtcttcctgt tccccccaaa acccaaggac actctcatga tctcccggac ccctgaggtc|780|
|acgtgcgtgg tggtggacgt gagccaggaa gaccccgagg tccagttcaa ctggtacgtg|840|
|gatggcgtgg aggtgcataa tgccaagaca aagccgcggg aggagcagtt caacagcacg|900|
|taccgtgtgg tcagcgtcct caccgtcctg caccaggact ggctgaacgg caaggagtac|960|
|aagtgcaagg tctccaacaa aggcctcccg tcctccatcg agaaaaccat ctccaaagcc|1020|
|aaagggcagc cccgagagcc acaggtgtac accctgcccc catcccagga ggagatgacc|1080|
|aagaaccagg tcagcctgac ctgcctggtc aaaggcttct accccagcga catcgccgtg|1140|
|gagtgggaga gcaatgggca gccggagaac aactacaaga ccacgcctcc cgtgctggac|1200|
|tccgacggct ccttcttcct ctacagcagg ctaaccgtgg acaagagcag gtggcaggag|1260|
|gggaatgtct tctcatgctc cgtgatgcat gaggctctgc acaaccacta cacacagaag|1320|
|agcctctccc tgtctctggg taaa|1344|

<210> SEQ ID NO 44
<211> LENGTH: 448
<212> TYPE: PRT

<213> ORGANISM: Artificial Sequence
<220> FEATURE:
<223> OTHER INFORMATION: Engineered immunoglobulin heavy chain sequence

<400> SEQUENCE: 44

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Ala Pro Lys Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

Ser Asp Gly Ser Phe Phe Leu Tyr Ser Arg Leu Thr Val Asp Lys Ser
385             390             395             400
                    405                 410                 415

Arg Trp Gln Glu Gly Asn Val Phe Ser Cys Ser Val Met His Glu Ala
                    420                 425                 430

Leu His Asn His Tyr Thr Gln Lys Ser Leu Ser Leu Ser Leu Gly Lys
                    435                 440                 445

```
<210> SEQ ID NO 45
<211> LENGTH: 1344
<212> TYPE: DNA
<213> ORGANISM: Artificial Sequence
<220> FEATURE:
<221> NAME/KEY: source
<222> LOCATION: 1..1344
<223> OTHER INFORMATION: /mol_type="unassigned DNA"
      /note="Engineered immunoglobulin heavy chain sequence"
      /organism="Artificial Sequence"

<400> SEQUENCE: 45
caggtccagc ttgtgcagtc tggggctgag gtgaagaagc ctggggcctc agtgaaggtt      60
tcctgcaagg catctggata cacattcact agctatgtga tgcactgggt gcgacaggcc     120
cctggacaag ggcttgagtg gatgggatat attaatcctt ataatgatgc tcctaaatac     180
aatgagaagt tcaaaggcag agtcaccatg accaggaca cgtccacgag cacagtctac      240
atggagctga gcagcctgag atctgaggac acggccgtgt attactgtgc gagaggcttg     300
ggttacgccc tttactatgc tatggactac tggggccaag gacaatggt caccgtctcg      360 agcgcatcca ccaagggccc atccgtcttc ccctggcgc cctgctccag gagcacctcc     420
gagagcacag ccgccctggg ctgcctggtc aaggactact ccccgaacc ggtgacggtg     480 tcgtggaact caggcgccct gaccagcggc gtgcacacct tcccggctgt cctacagtcc     540
tcaggactct actccctcag cagcgtggtg accgtgccct ccagcagctt gggcacgaag     600
acctacacct gcaacgtaga tcacaagccc agcaacacca aggtggacaa gagagttgag     660
tccaaatatg gtccccccatg cccaccatgc ccagcacctg agttcctggg gggaccatca     720
gtcttcctgt tccccccaaa acccaaggac actctcatga tctcccggac ccctgaggtc     780
acgtgcgtgg tggtggacgt gagccaggaa gaccccgagg tccagttcaa ctggtacgtg     840
gatggcgtgg aggtgcataa tgccaagaca agccgcggg aggagcagtt caacagcacg     900
taccgtgtgg tcagcgtcct caccgtcctg caccaggact ggctgaacgg caaggagtac     960
aagtgcaagg tctccaacaa aggcctcccg tcctccatcg agaaaaccat ctccaaagcc    1020
aaagggcagc cccgagagcc acaggtgtac accctgcccc catcccagga ggagatgacc    1080
aagaaccagg tcagcctgac ctgcctggtc aaaggcttct accccagcga catcgccgtg    1140
gagtgggaga gcaatgggca gccggagaac aactacaaga ccacgcctcc cgtgctggac    1200
tccgacggct ccttcttcct ctacagcagg ctaaccgtgg acaagagcag gtggcaggag    1260
gggaatgtct tctcatgctc cgtgatgcat gaggctctgc acaaccacta cacacagaag    1320
agcctctccc tgtctctggg taaa                                           1344

<210> SEQ ID NO 46
<211> LENGTH: 448
<212> TYPE: PRT
<213> ORGANISM: Artificial Sequence
<220> FEATURE:
<223> OTHER INFORMATION: Engineered immunoglobulin heavy chain sequence
```

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Ala Pro Lys Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 47
<211> LENGTH: 1344
<212> TYPE: DNA
<213> ORGANISM: Artificial Sequence
<220> FEATURE:
<221> NAME/KEY: source
<222> LOCATION: 1..1344
<223> OTHER INFORMATION: /mol_type="unassigned DNA"
      /note="Engineered immunoglobulin heavy chain sequence"
      /organism="Artificial Sequence"

<400> SEQUENCE: 47
caggtccagc ttgtgcagtc tgggctgag gtgaagaagc ccggcgccag cgtgaaggtg    60
agctgcaagg ccagcggata cacattcact agctatgtga tgcactgggt gagacaggcc   120
cccggccagg gcctggagtg gatgggctat attaatcctt ataatgatgc tcctaaatac   180
aatgagaagt tcaaaggcag agtgaccatg accagagaca ccagcgccag caccgcctac   240
atggagctga gcagcctgag aagcgacgac accgccgtgt actactgcgc cagaggcttg   300
ggttacgccc tttactatgc tatggactac tggggccagg gcaccaccgt gaccgtgagc   360
agcgcatcca ccaagggccc atccgtcttc cccctggcgc cctgctccag gagcacctcc   420
gagagcacag ccgccctggg ctgcctggtc aaggactact ccccgaacc ggtgacggtg   480 tcgtggaact caggcgccct gaccagcggc gtgcacacct tcccggctgt cctacagtcc   540
tcaggactct actccctcag cagcgtggtg accgtgccct ccagcagctt gggcacgaag   600
acctacacct gcaacgtaga tcacaagccc agcaacacca aggtggacaa gagagttgag   660
tccaaatatg gtccccccatg cccaccatgc ccagcacctg agttcctggg gggaccatca   720
gtcttcctgt tccccccaaa acccaaggac actctcatga tctcccggac ccctgaggtc   780
acgtgcgtgg tggtggacgt gagccaggaa gaccccgagg tccagttcaa ctggtacgtg   840
gatggcgtgg aggtgcataa tgccaagaca aagccgcggg aggagcagtt caacagcacg   900
taccgtgtgg tcagcgtcct caccgtcctg caccaggact ggctgaacgg caaggagtac   960
aagtgcaagg tctccaacaa aggcctcccg tcctccatcg agaaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
tccgacggct ccttcttcct ctacagcagg ctaaccgtgg acaagagcag gtggcaggag  1260
gggaatgtct tctcatgctc cgtgatgcat gaggctctgc acaaccacta cacacagaag  1320
agcctctccc tgtctctggg taaa                                         1344

<210> SEQ ID NO 48
<211> LENGTH: 448
<212> TYPE: PRT
<213> ORGANISM: Artificial Sequence
<220> FEATURE:
<223> OTHER INFORMATION: Engineered immunoglobulin heavy chain sequence

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
            35                  40                  45

Gly Tyr Ile Asn Pro Tyr Asn Asp Ala Pro Lys Tyr Asn Glu Lys Phe
50                  55                  60

Lys Gly Arg Val Thr Met Thr Arg Asp Thr Ser Ala Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Leu Gly Tyr Ala Leu Tyr Tyr Ala Met Asp Tyr Trp Gly
                100                 105                 110

Gln Gly Thr Thr Val Thr Val Ser Ser Ala Ser Thr Lys Gly Pro Ser
                115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
        435                 440                 445

<210> SEQ ID NO 49
<211> LENGTH: 642
<212> TYPE: DNA
<213> ORGANISM: Artificial Sequence
<220> FEATURE:
<221> NAME/KEY: source
<222> LOCATION: 1..642
<223> OTHER INFORMATION: /mol_type="unassigned DNA"
      /note="Engineered immunoglobulin light chain sequence"
      /organism="Artificial Sequence"

<400> SEQUENCE: 49
gacattgtga tgacccagtc tccttccact ctctctgcat ctgtgggaga cagagtaacc    60
atcacttgca aggccagtca gaatgtgggt aataatgtag cctggtatca gcagaaacca   120
gggaaagccc ctaagctact gatctcttcc gcatccaacc gggacagtgg tgtgccctca   180
aggtttagcg gcagtggatc agggacagag ttcacattga ccatatccag cctgcagcct   240
gatgattttg ctacttattt ctgccaacaa tataacattt acccattcac gtttggccag   300
ggcaccaagc tagagatcaa acggacggtt gctgcaccct ctgtctttat cttcccgcca   360
tctgatgaac agttgaagtc cggaacagcc tctgttgtgt gcctgctgaa taactttat    420
ccccgcgagg cgaaagttca gtggaaggtg gataacgccc tccaatcagg caattcccag   480
gagagtgtga cagagcaaga ttccaaggac tcaacctaca gcctcagcag tactttaact   540
ctgagcaaag cagactacga gaagcacaaa gtctacgctt gcgaagtcac ccatcagggc   600
cttagctcgc ccgtcacaaa gagctttaac aggggagaat gt                      642

<210> SEQ ID NO 50
<211> LENGTH: 214
<212> TYPE: PRT
<213> ORGANISM: Artificial Sequence
<220> FEATURE:
<223> OTHER INFORMATION: Engineered immunoglobulin light chain sequence

<400> SEQUENCE: 50

Asp Ile Val Met Thr Gln Ser Pro Ser Thr Leu Ser Ala Ser Val Gly
1               5                   10                  15

Asp Arg Val Thr Ile Thr Cys Lys Ala Ser Gln Asn Val Gly Asn Asn
            20                  25                  30

Val Ala Trp Tyr Gln Gln Lys Pro Gly Lys Ala Pro Lys Leu Leu Ile
        35                  40                  45

Ser Ser Ala Ser Asn Arg Asp Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Asn Ile Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 1344
<212> TYPE: DNA
<213> ORGANISM: Artificial Sequence
<220> FEATURE:
<221> NAME/KEY: source
<222> LOCATION: 1..1344
<223> OTHER INFORMATION: /mol_type="unassigned DNA"
      /note="Engineered immunoglobulin heavy chain sequence"
      /organism="Artificial Sequence"

<400> SEQUENCE: 51

```
caggtccaac ttgtgcagtc tggggctgaa gtgaagaagc ccggcgctag tgtgaaggtt      60
tcatgtaagg cttctggata cacatttact tcatatgtaa tgcactgggt gcgtcaagcc     120
cctggccagg gcctggagtg gatgggggtat attaatcctt ataatgatgc tcctaaatac    180
aatgagaagt tcaaaggaaa agcaactatg accagtgata ctagcgcttc aaccgcctac    240
atggagctga gcagcttaag aagcgacgac accgccgtgt actattgtgc caggggcttg    300
ggttacgccc tttattatgc tatggactac tggggtcagg gcaccacagt gaccgttagc    360
tctgcatcta ctaagggacc atccgtcttc ccctggcgc catgctcccg cagtacaagt     420
gagagcacag cagccctggg ctgtttggta aaggactact cccccgaacc tgtgactgtg    480
tcttggaact caggcgcccct gactagcggc gtgcacactt ccctgctgt cctacagtcc    540
tcaggactat actccctctc gtctgtggtg acagtgcctt cctcatcatt gggaacgaaa    600
acctatactt gcaacgttga tcacaagccc agcaacacca aggtggacaa gagagttgag    660
tccaaatatg gtccccccatg tccaccatgt ccagcacctg agtttcttgg cggaccaagt    720
gttttcctgt tccccccaaa acccaaggat actctcatga taagtcgcac ccctgaagtc    780
acttgcgtgg tggtggacgt tagccaggaa gatcccgaag tccaattcaa ctggtacgta    840
gatggcgtag aagtgcataa tgcgaagaca aagccgagag aggagcagtt taattcgacg    900
tatcgggtgg tcagcgtcct cacagtcctg caccaggact ggctgaacgg caaggagtat    960
aagtgcaagg tctccaacaa aggtctcccg tcctccattg agaaacaat ctccaaagca     1020
aaagggcagc cccgagaacc acaagtgtac accctgcccc catctcagga ggagatgacc    1080
aagaaccagg tcagtcttac ctgcctggtc aaaggctttt atccctcaga tatcgccgtt    1140
gagtgggaaa gcaatgggca gccggagaac aactacaaga ccacgcctcc cgttctggat    1200
tctgacggat cgttcttttt atacagcagg ctaaccgtgg acaagtctcg gtggcaggaa    1260
gggaatgtat tttcttgcag tgtaatgcat gaggctctgc acaatcatta cacacagaag    1320
tctctctccc tgtctcttgg taaa                                            1344
```

<210> SEQ ID NO 52
<211> LENGTH: 448
<212> TYPE: PRT
<213> ORGANISM: Artificial Sequence
<220> FEATURE:
<223> OTHER INFORMATION: Engineered immunoglobulin heavy chain sequence

<400> SEQUENCE: 52

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Val Met His Trp Val Arg Gln Ala Pro Gly Gln Gly Leu Glu Trp Met
        35                  40                  45
Gly Tyr Ile Asn Pro Tyr Asn Asp Ala Pro Lys Tyr Asn Glu Lys Phe
    50                  55                  60
Lys Gly Lys Ala Thr Met Thr Ser Asp Thr Ser Ala Ser Thr Ala Tyr
65                  70                  75                  80
Met Glu Leu Ser Ser Leu Arg Ser Asp Asp Thr Ala Val Tyr Tyr Cys
                85                  90                  95
Ala Arg Gly Leu Gly Tyr Ala Leu Tyr Tyr Ala Met Asp Tyr Trp Gly
            100                 105                 110
Gln Gly Thr Thr Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
    210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
```

405                 410                 415
Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 53
<211> LENGTH: 1335
<212> TYPE: DNA
<213> ORGANISM: Mus musculus
<220> FEATURE:
<221> NAME/KEY: source
<222> LOCATION: 1..1335
<223> OTHER INFORMATION: /mol_type="unassigned DNA"
      /organism="Mus musculus"

<400> SEQUENCE: 53
gaggtccagt tgcagcagtc tggacctgag ctggtaaagc ctggggcttc agtgaagatg      60
tcctgcaagg cttctggata cacattcact agctatgtga tgcactgggt gaagcagaag     120
cctgggcagg gccttgagtg gattggatat attaatcctt ataatgatgc tcctaaatac     180
aatgagaagt tcaaaggcaa ggccacagtg acttcagaca gtcctccgg cacagcctac      240 atggagctca gcagcctgac ctctgaggac tctgcggtct attactgtgc aaggggcttg     300
ggttacgccc tttactatgc tatggactac tggggtcaag aacctcagt caccgtctcc      360 tcagccaaaa cgacaccccc atctgtctat ccactggccc ctggatctgc tgcccaaact     420
aactccatgg tgaccctggg atgcctggtc aagggctatt tccctgagcc agtgacagtg     480
acctggaact ctgatcccct gtccagcggt gtgcacacct tcccagctgt cctggagtct     540
gacctctaca ctctgagcag ctcagtgact gtccccctcca gccctcggcc cagcgagacc     600
gtcacctgca acgttgccca cccggccagc agcaccaagg tggacaagaa aattgtgccc     660
agggattgtg gttgtaagcc ttgcatatgt acagtcccag aagtatcatc tgtcttcatc     720 ttcccccaa agcccaagga tgtgctcacc attactctga ctcctaaggt cacgtgtgtt     780
gtggtagaca tcagcaagga tgatcccgag gtccagttca gctggtttgt agatgatgtg     840
gaggtgcaca cagctcagac gcaacccgg gaggagcagt tcaacagcac tttccgctca     900
gtcagtgaac ttcccatcat gcaccaggac tggctcaatg gcaaggagtt caaatgcagg     960
gtcaacagtg cagcttttcc tgcccccatc gagaaaacca tctccaaaac caaaggcaga    1020
ccgaaggctc cacaggtgta caccattcca cctcccaagg agcagatggc caaggataaa    1080
gtcagtctga cctgcatgat aacagacttc ttccctgaag acattactgt ggagtggcag    1140
tggaatgggc agccagcgga gaactacaag aacactcagc ccatcatgaa cacgaatggc    1200
tcttacttcg tctacagcaa gctcaatgtg cagaagagca ctgggaggc aggaaatact    1260 ttcacctgct ctgtgttaca tgagggcctg cacaaccacc atactgagaa gagcctctcc    1320
cactctcctg gtaaa                                                     1335

<210> SEQ ID NO 54
<211> LENGTH: 642
<212> TYPE: DNA
<213> ORGANISM: Mus musculus
<220> FEATURE:
<221> NAME/KEY: source
<222> LOCATION: 1..642
<223> OTHER INFORMATION: /mol_type="unassigned DNA"
      /organism="Mus musculus"

<400> SEQUENCE: 54

-continued

```
gacattgtga tgacccagtc tcaaaaattc aagtccacat cagtaggaga cagggtcagc    60
gtcacctgca aggccagtca gaatgtgggt aataatgtag cctggtatca acagaaagca   120
gggcaatctc ctaaagcact gatttcctcg gcatccaacc gtgacagtgg agtccctgat   180
cgcttcacag gcagtggatc tgggacagat ttcactctca ccatcagcaa tgtgcagtct   240
gaagacttgg cagactattt ctgtcagcaa tataacatct atccattcac gttcggctcg   300
gggacaaagt tggaaataaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctatacct gtgaggccac tcacaagaca   600
tcaacttcac ccattgtcaa gagcttcaac aggaatgagt gt                      642
```

<210> SEQ ID NO 55
<211> LENGTH: 445
<212> TYPE: PRT
<213> ORGANISM: Mus musculus

<400> SEQUENCE: 55

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Ala Pro Lys Tyr Asn Glu Lys Phe
    50                  55                  60

Lys Gly Lys Ala Thr Val Thr Ser Asp Lys Ser Ser Gly Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Glu Ser Asp Leu Tyr Thr Leu Ser Ser Ser Val Thr Val Pro
            180                 185                 190

Ser Ser Pro Arg Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255
```

Val Thr Cys Val Val Asp Ile Ser Lys Asp Pro Glu Val Gln
            260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
            325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
            370                 375                 380

Pro Ala Glu Asn Tyr Lys Asn Thr Gln Pro Ile Met Asn Thr Asn Gly
385                 390                 395                 400

Ser Tyr Phe Val Tyr Ser Lys Leu Asn Val Gln Lys Ser Asn Trp Glu
            405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 56
<211> LENGTH: 214
<212> TYPE: PRT
<213> ORGANISM: Mus musculus

<400> SEQUENCE: 56

Asp Ile Val Met Thr Gln Ser Gln Lys Phe Lys Ser Thr Ser Val Gly
1               5                   10                  15

Asp Arg Val Ser Val Thr Cys Lys Ala Ser Gln Asn Val Gly Asn Asn
            20                  25                  30

Val Ala Trp Tyr Gln Gln Lys Ala Gly Gln Ser Pro Lys Ala Leu Ile
        35                  40                  45

Ser Ser Ala Ser Asn Arg Asp Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ile Tyr Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

```
Thr Cys Glu Ala Thr His Lys Thr Ser Thr Ser Pro Ile Val Lys Ser
        195                 200                 205

Phe Asn Arg Asn Glu Cys
    210

<210> SEQ ID NO 57
<211> LENGTH: 57
<212> TYPE: DNA
<213> ORGANISM: Homo sapiens
<220> FEATURE:
<221> NAME/KEY: source
<222> LOCATION: 1..57
<223> OTHER INFORMATION: /mol_type="unassigned DNA"
      /organism="Homo sapiens"

<400> SEQUENCE: 57
atggactgga cctggaggat cctcttttg gtggcagcag ccacaggtgc ccactcc        57

<210> SEQ ID NO 58
<211> LENGTH: 19
<212> TYPE: PRT
<213> ORGANISM: Homo sapiens

<400> SEQUENCE: 58

Met Asp Trp Thr Trp Arg Ile Leu Phe Leu Val Ala Ala Ala Thr Gly
1               5                   10                  15

Ala His Ser

<210> SEQ ID NO 59
<211> LENGTH: 66
<212> TYPE: DNA
<213> ORGANISM: Homo sapiens
<220> FEATURE:
<221> NAME/KEY: source
<222> LOCATION: 1..66
<223> OTHER INFORMATION: /mol_type="unassigned DNA"
      /organism="Homo sapiens"

<400> SEQUENCE: 59
atggacatga gagtcctcgc tcagctcctg gggctcctgc tgctctgttt cccaggtgcc    60
agatgt                                                              66

<210> SEQ ID NO 60
<211> LENGTH: 22
<212> TYPE: PRT
<213> ORGANISM: Homo sapiens

<400> SEQUENCE: 60

Met Asp Met Arg Val Leu Ala Gln Leu Leu Gly Leu Leu Leu Leu Cys
1               5                   10                  15

Phe Pro Gly Ala Arg Cys
            20
```